(12) United States Patent
Watanabe et al.

(10) Patent No.: US 6,527,928 B1
(45) Date of Patent: *Mar. 4, 2003

(54) HEATER-EQUIPPED AIR-FUEL RATIO SENSOR

(75) Inventors: Isao Watanabe, Nagoya (JP); Michihiro Yamakawa, Kariya (JP); Masanori Fukutani, Nagoya (JP)

(73) Assignee: Denso Corporation (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/360,148

(22) Filed: Jul. 26, 1999

Related U.S. Application Data

(62) Division of application No. 08/789,187, filed on Jan. 24, 1997, now Pat. No. 5,956,841.

(30) Foreign Application Priority Data

Jan. 25, 1996 (JP) .............................. 8-032893

(51) Int. Cl.$^7$ ............................ G01N 27/407
(52) U.S. Cl. ................ 204/424; 204/408; 204/427; 204/428
(58) Field of Search ................ 204/408, 421–429; 205/785

(56) References Cited

U.S. PATENT DOCUMENTS

| | | |
|---|---|---|
| 4,528,086 A | 7/1985 | Kato et al. .................. 204/427 |
| 4,540,479 A | 9/1985 | Sakurai et al. |
| 4,556,475 A * | 12/1985 | Bayha et al. ................ 204/427 |
| 4,578,174 A * | 3/1986 | Kato et al. .................... 204/427 |
| 4,741,816 A | 5/1988 | Nishio et al. |
| 4,824,550 A * | 4/1989 | Ker et al. ..................... 204/427 |
| 5,098,548 A * | 3/1992 | Duce .......................... 204/424 |
| 5,451,748 A * | 9/1995 | Matsuzaki et al. .......... 219/543 |
| 5,679,226 A * | 10/1997 | Furusaki et al. ............. 204/427 |
| 5,759,365 A * | 6/1998 | Yamada et al. .............. 204/427 |

FOREIGN PATENT DOCUMENTS

| | | |
|---|---|---|
| JP | 60-137364 | 9/1985 |
| JP | 5-046498 | 4/1993 |
| JP | 6-003430 | 1/1994 |
| JP | 6-242064 | 9/1994 |

* cited by examiner

Primary Examiner—T. Tung
(74) Attorney, Agent, or Firm—Nixon & Vanderhye PC

(57) ABSTRACT

A heater is inserted into an inside chamber of a sensor element until a tip end of the heater is surely brought into contact with a bottom surface of the inside chamber. Next, a metallic holder is attached on an outside surface of the heater. Then, the metallic holder is slid along the outside surface of the heater toward the bottom surface of the sensor element to engage the metallic holder with an edge of the sensor element.

29 Claims, 16 Drawing Sheets

FIG. 1A
FIG. 1B
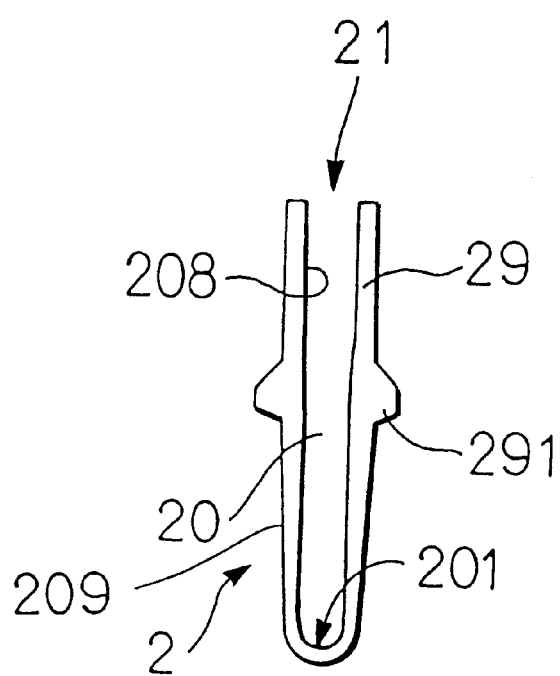
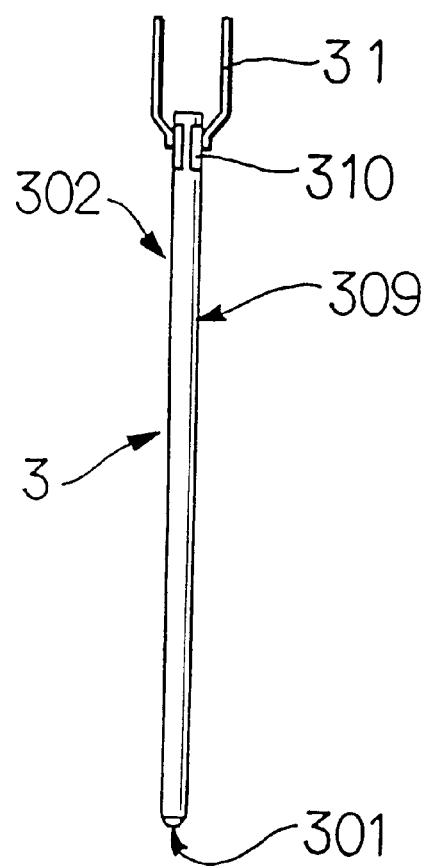

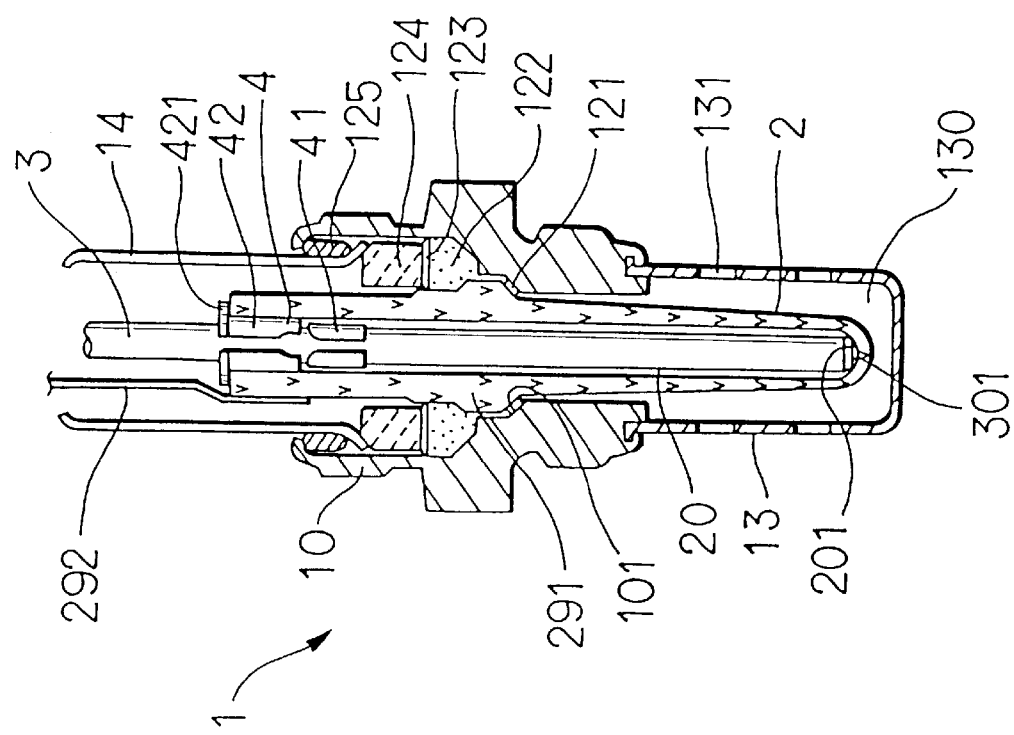
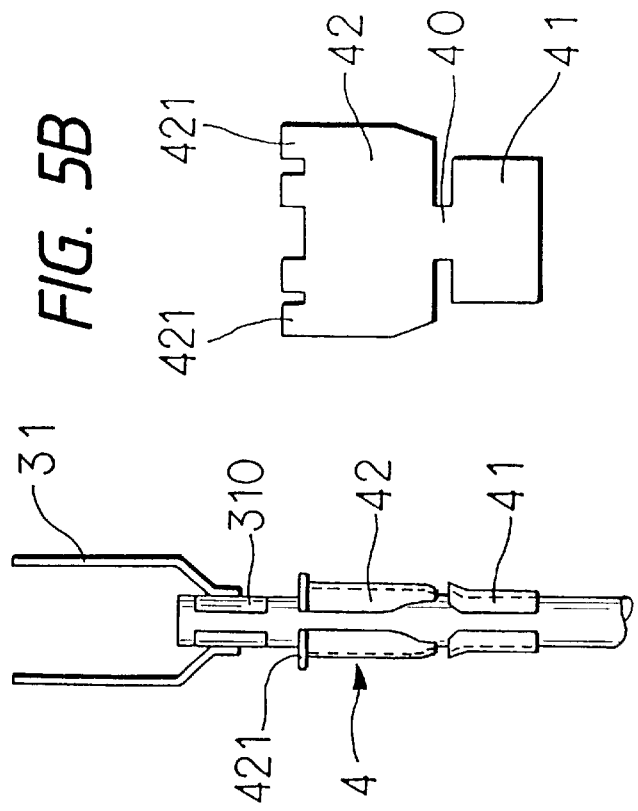

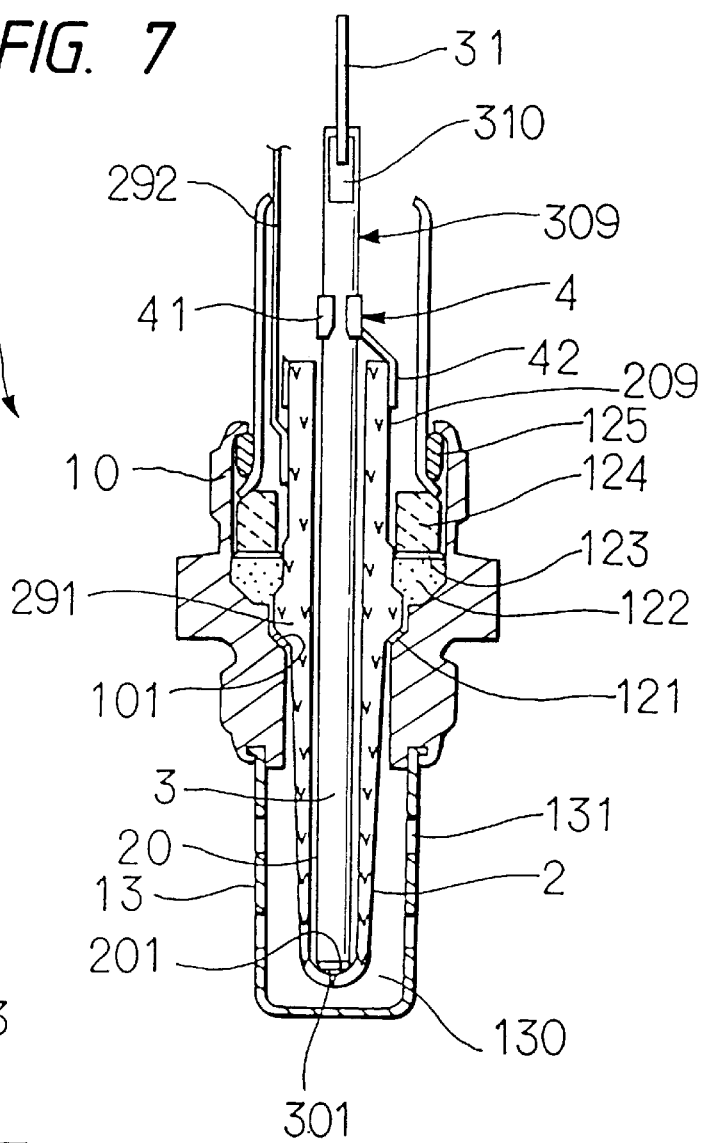
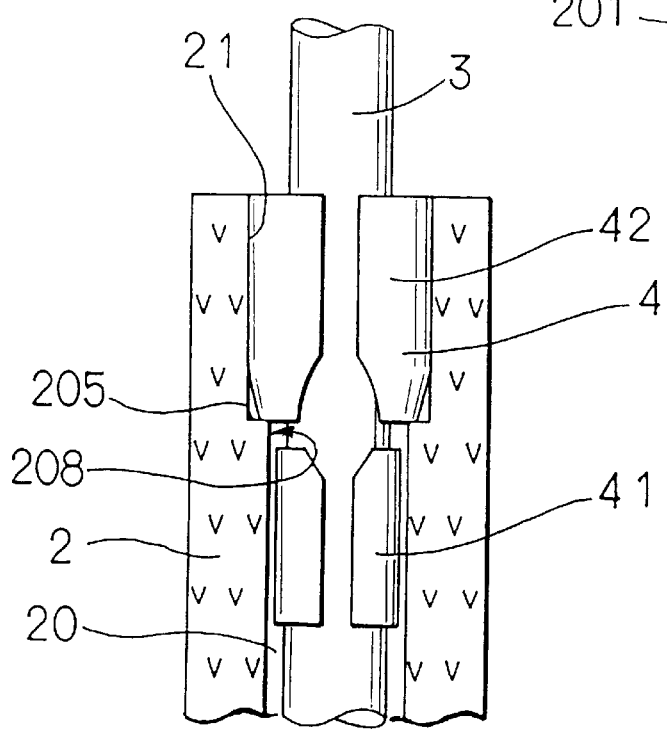

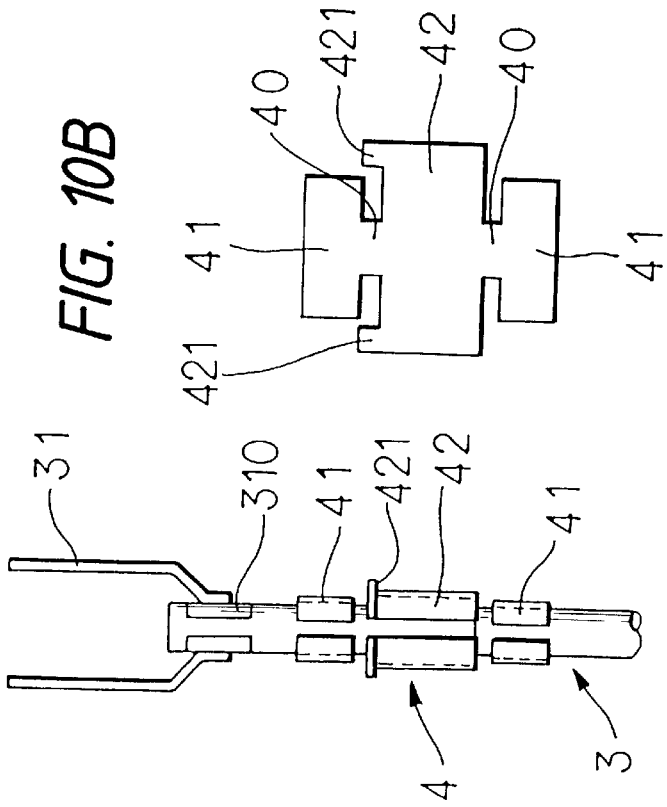
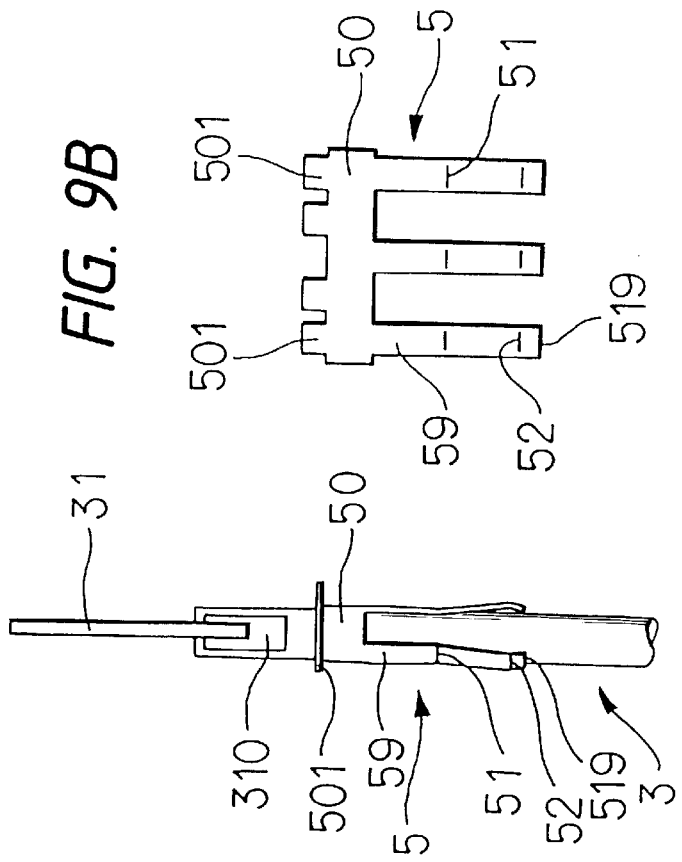

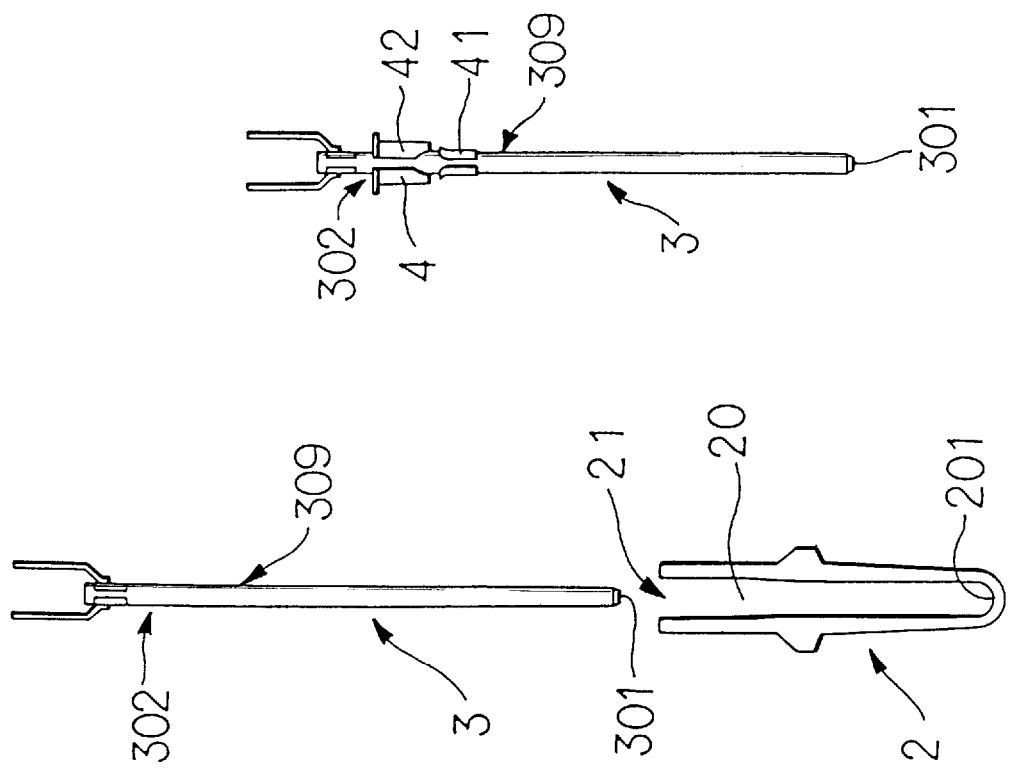

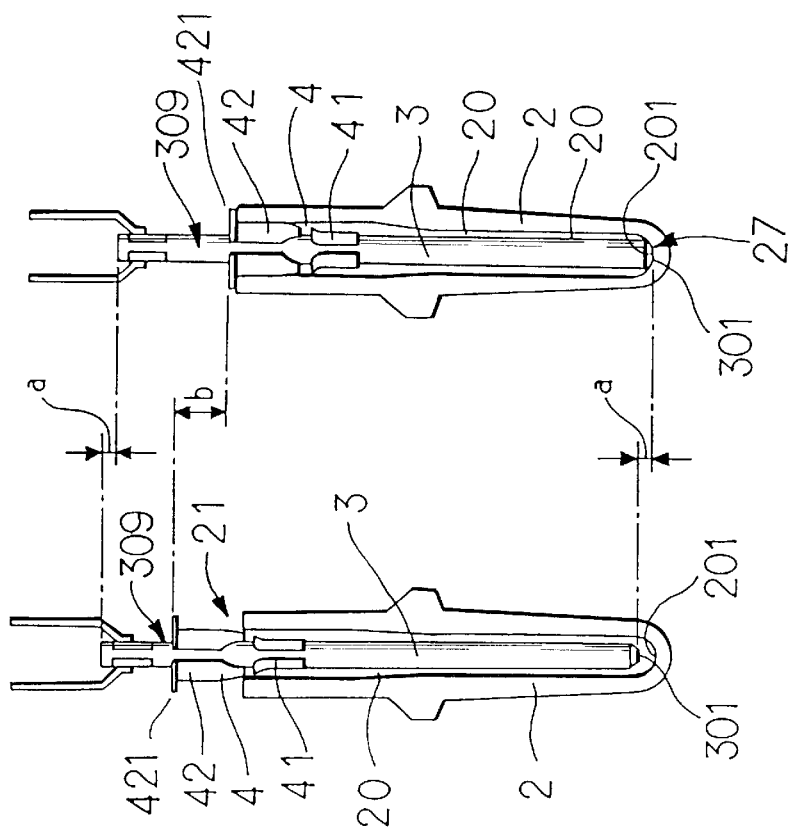
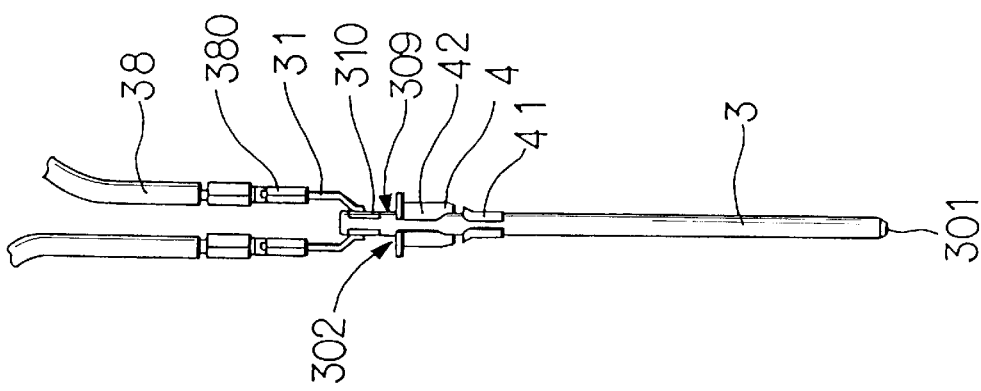

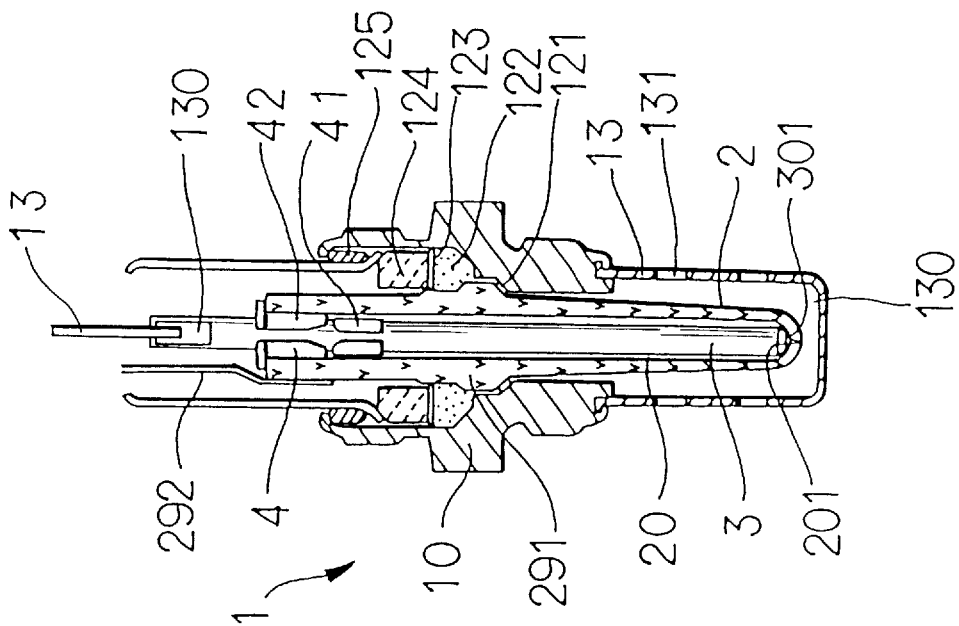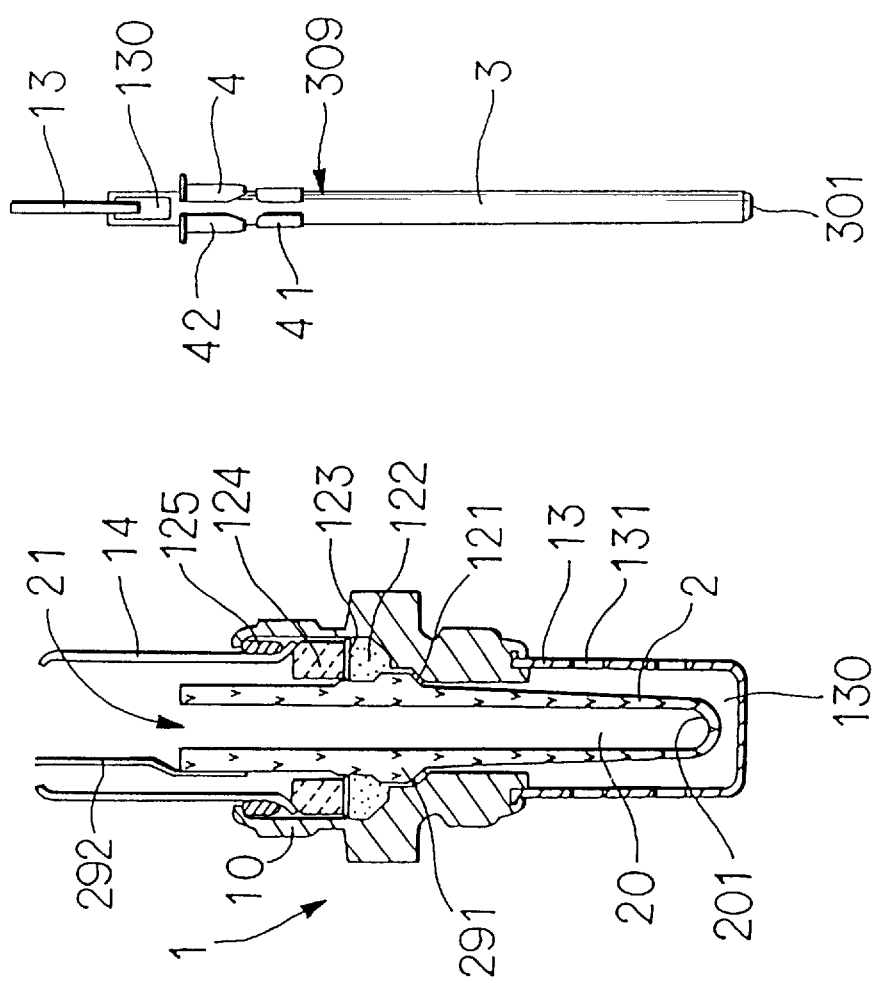

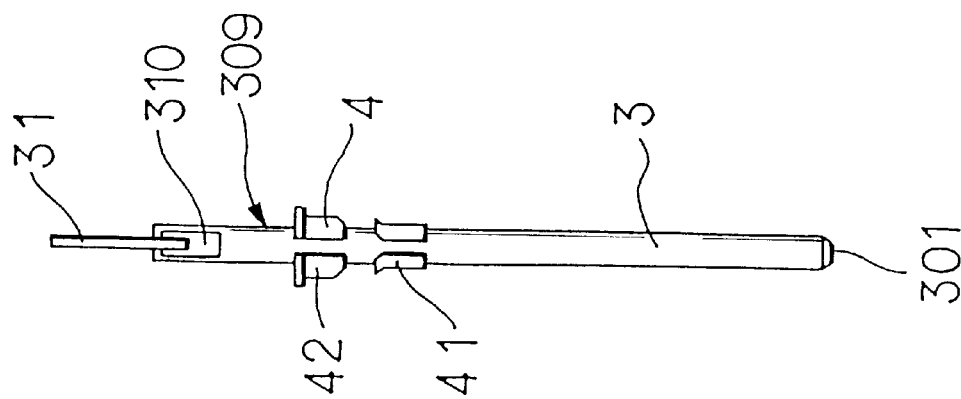
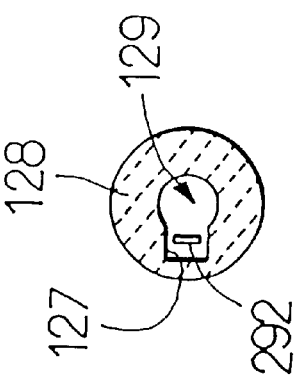
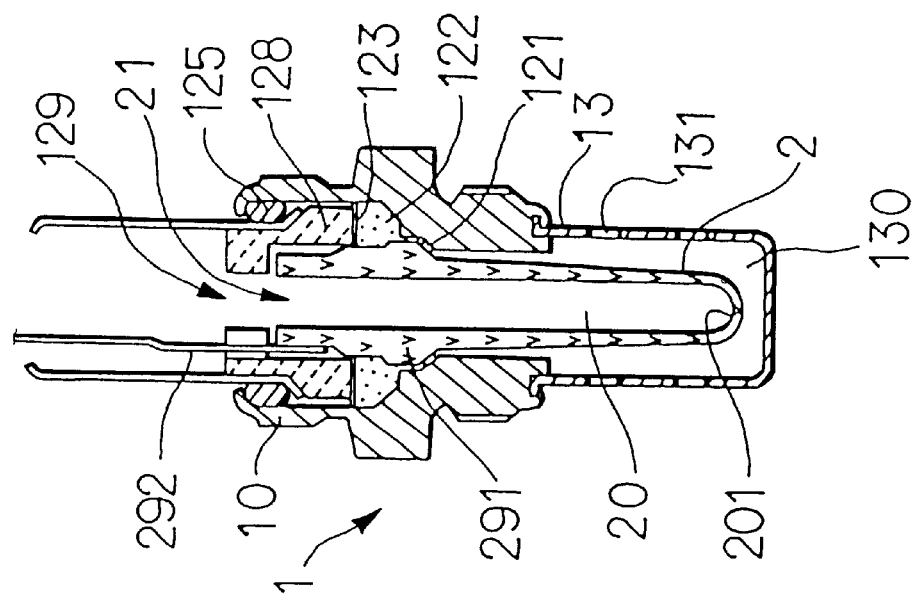

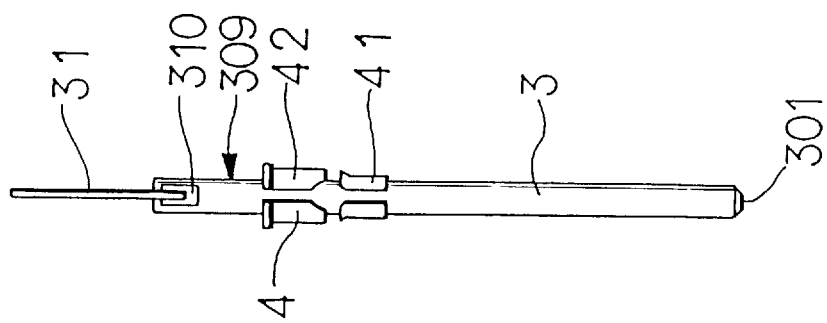
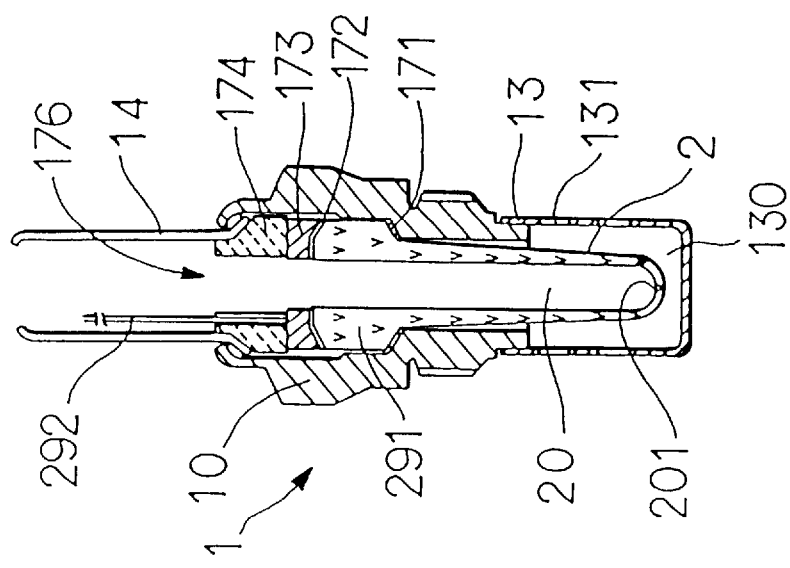
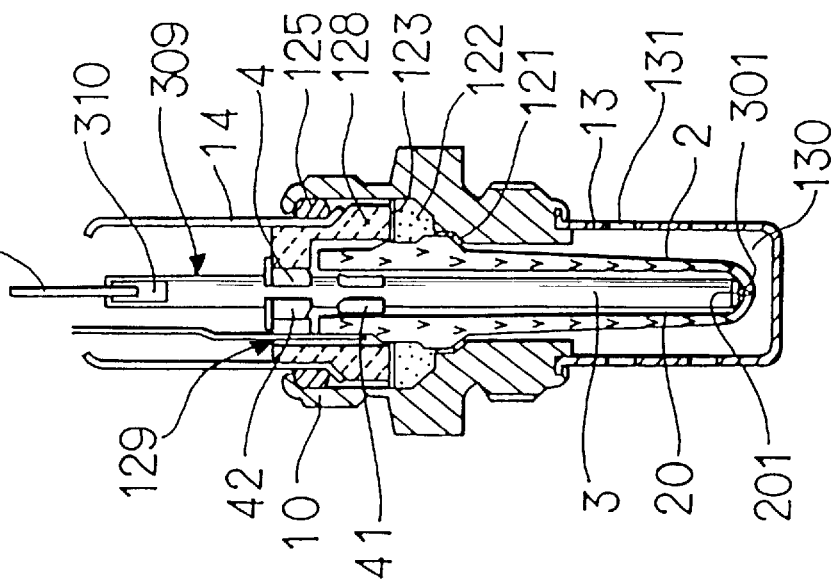

HEATER-EQUIPPED AIR-FUEL RATIO SENSOR

This application is a division of application Ser. No. 08/789,187 filed Jan. 24, 1997 now U.S. Pat. No. 5,956,841.

BACKGROUND OF THE INVENTION

1. Field of the Invention

The present invention relates to a method for assembling a heater-equipped air-fuel ratio sensor, which is preferably installed on an exhaust gas emission system of an internal combustion engine for automotive vehicles and others.

2. Related Art

In general, to improve the exhaust gas purification efficiency, an air-fuel ratio of exhaust gas is sensed by an air-fuel ratio sensor, such as an oxygen ($O_2$) sensor. An air-fuel ratio sensor usually comprises a cylindrical or cup-shaped sensor element having an open end and an opposed closed end with an inside chamber. A stick-like heater is inserted in the inside chamber of this sensor element.

The heater is necessary to warm up the sensor element quickly to its active temperature during an engine start-up condition where the engine is operated at a low temperature.

More specifically, a portion sensing an air-fuel ratio of exhaust gas is a particular portion of the sensor element which is subjected to the exhaust gas (i.e. gas to be sensed), normally the front end of the sensor element. Accordingly, in the detection of the air-fuel ratio, it is definitely necessary to heat up the sensitive portion of the air-fuel ratio sensor to its active temperature. Without this warmup operation, the sensor element cannot operate accurately nor its characteristics is stabilized.

For example, Japanese Patent No. 5-46498, published in 1993, discloses this kind of air-fuel ratio sensor. According to this prior art, a heater is united with a fixing metal by soldering and the fixing metal is fixed to the open end of an inside chamber by means of a coil spring.

Furthermore, Japanese Patent No. 6-3430, published in 1994, discloses another air-fuel ratio sensor. According to this prior art, a heater is fixed to an inside chamber by utilizing a fixing metal, although the heater and the fixing metal are not united.

Meanwhile, to satisfy the exhaust gas emission requirements strictly regulated year by year, it is required to detect an air-fuel ratio within a short time period even immediately after an engine is just started up. One measure for solving this requirement is to dispose a heater as close as possible to the sensitive edge of the sensor element. By doing so, heat generated from the heater is effectively used to warm up the sensitive edge of the sensor element. More specifically, it is most preferable to bring the tip end of the heater into contact with the bottom surface of the inside chamber and to keep the contact between the heater and the bottom surface.

However, there are following problems in assembling the heater in the sensor element.

There is a necessity of checking or confirming during the assembling operation that the tip end of the heater is surely brought into contact with the bottom surface of the inside chamber.

Both of the sensor element and the heater are fragile and weak against shock. Hence, if the heater is forcibly inserted into the inside chamber of the sensor element by applying an excessively large force, there will be a possibility that either the sensor element or the heater is damaged.

SUMMARY OF THE INVENTION

Accordingly, in view of above-described problems encountered in the related art, a principal object of the present invention is to provide an improved method for assembling a heater-equipped air-fuel sensor which is capable of surely bringing the tip end of a heater into contact with the bottom surface of an inside chamber of a sensor element without damaging the heater and the sensor element.

In order to accomplish this and other related objects, the present invention provides a novel and excellent assembling method for a heater-equipped air-fuel ratio sensor having various aspects as described hereinafter.

A first aspect of the present invention provides an method for assembling a heater-equipped air-fuel ratio sensor which comprises a cylindrical sensor element having an open end and an opposed closed end with an inside chamber defined therein and a stick-like heater inserted in the inside chamber of the sensor element so that a tip end of the heater is brought into contact with a bottom surface of the inside chamber, and the heater is supported to the sensor element by a metallic holder.

More specifically, the first aspect assembling method comprises the steps of inserting the heater into the inside chamber of the sensor element until the tip end of the heater is brought into contact with the bottom surface of the inside chamber, and sliding the metallic holder along an outside surface of the heater toward the bottom surface of the inside chamber until the metallic holder is engaged with the sensor element.

A function of the above-described first aspect assembling method will be explained hereinafter.

According to the first aspect assembling method, the stick-like heater is inserted into the inside chamber of the sensor element so that the tip end of the heater can be brought into contact with the bottom surface of the inside chamber. Then, the metallic holder is fixed to the sensor element.

Accordingly, it becomes possible to prevent the heater from interfering with other components of this air-fuel ratio sensor, and therefore it becomes possible to bring the tip end of the heater safely into contact with the bottom surface of the inside chamber. In other words, the heater can be smoothly installed to a predetermined position in the sensor element.

Then, the metallic holder is elastically installed on the heater under the condition where the heater keeps contact with the bottom surface of the inside chamber.

Next, the metallic holder slides along the outer surface of the heater and shifts toward the bottom surface of the sensor element. When the metallic holder is slid along the outer surface of the heater, a sliding frictional force is caused between a heater holding portion (described later) and the outer surface of the heater. With this sliding frictional force, the heater can be firmly pressed to the bottom surface of the inside chamber. The contact between the tip end of the heater and the bottom surface of the inside chamber is maintained until the metallic holder is fixed to the open end of the sensor element. Accordingly, the tip end of the heater is surely fixed while keeping contact with the bottom surface of the inside chamber.

As described above, a force acting on the bottom surface of the sensor element is substantially equivalent to a pressing force acting in the axial direction by the above-described sliding frictional force. Thus, the heater can be fixed in the inside chamber with its tip end kept in firm contact with bottom surface of the inside chamber without adding an excessive force to the sensor element. Furthermore, the sensor element and the heater can be surely prevented from being damaged during their assembly.

According to the above-described first aspect of the invention, it becomes possible to provide an assembling method for a heater-equipped air-fuel ratio sensor which is capable of surely bringing the tip end of the heater into contact with the bottom surface of the inside chamber of the sensor element, without damaging the sensor element and the heater during their assembly.

Next, it is possible to install the metallic holder to the sensor element at an intermediate portion of the wall of the inside chamber between the bottom surface and a open end (described below).

Furthermore, it is possible to fix the metallic holder to the open end region of the sensor element. In this case, the open end region the sensor element includes both of inside and outside surfaces of the sensor element as well as the opened top surface of the sensor element.

Even further, it is preferable to provide a tapered portion or a shoulder portion somewhere in the open end region or on the wall of the inside chamber of the sensor element for supporting the metallic holder.

According to preferred embodiments of the present invention, it is preferable that the above-described first aspect assembling method further comprise a step of installing the metallic holder elastically on an upper portion of the heater after the heater is inserted into the inside chamber of the sensor element.

That is, when the heater is assembled with the sensor element, the heater is first inserted into the inside chamber so that the tip end of the heater is brought into contact with the bottom surface of the inside chamber. Then, the metallic holder is elastically attached on the upper portion of the heater. Then, the metallic holder is slid along the outside surface of the heater toward the bottom surface of the sensor element. And, the metallic holder is fixed to the sensor element. With this assembling operation, the tip end of the heater can be surely brought into contact with or settled on the bottom surface of the sensor element.

Alternatively, it is preferable that the above-described first aspect assembling method further comprise a step of installing the metallic holder elastically on an upper portion of the heater in advance, before the heater is inserted into the inside chamber of the sensor element.

That is, when the heater is assembled with the sensor element, the metallic holder is elastically attached on the upper portion of the heater. Then, the heater is inserted into the inside chamber so that the tip end of the heater is brought into contact with the bottom surface of the inside chamber. Then, the metallic holder is slid along the outside surface of the heater toward the bottom surface of the sensor element. And, the metallic holder is fixed to the sensor element. With this assembling operation, the installation of metallic holder can be simplified.

Next, a second aspect of the present invention provides an assembling method for a heater-equipped air-fuel ratio sensor which comprises a cylindrical sensor element having an open end and an opposed closed end with an inside chamber defined therein and a stick-like heater inserted in the inside chamber of the sensor element so that a tip end of the heater is brought into contact with a bottom surface of the inside chamber, and the heater is supported to the sensor element by a metallic holder.

More specifically, the second aspect assembling method comprises the steps of installing the metallic holder elastically on an upper portion of the heater, inserting the heater into the inside chamber of the sensor element until the metallic holder is brought into contact with the sensor element under a condition where the tip end of the heater is not brought into contact with the bottom surface of the inside chamber, shifting the metallic holder toward the bottom surface of the inside chamber so that the heater held by the metallic holder is further inserted in the inside chamber and the tip end of the heater is brought into contact with the bottom surface of the inside chamber of the sensor element; and sliding the metallic holder along an outside surface of the heater toward the bottom surface of the inside chamber until the metallic holder is engaged with the sensor element.

In this case, the following relationship is established $$a<b$$

where "a" represents an axial clearance between the tip end of the heater and the bottom surface of the inside chamber at a moment the metallic holder is brought into contact with the sensor element, while "b" represents an axial shift distance of the metallic holder with respect to the outside surface of the heater.

According to the above-described second aspect assembling method, after the heater is inserted into the inside chamber, the metallic holder abuts the sensor element. Thereafter, the metallic holder is depressed, until the tip end of the heater is brought into contact with or settled on the bottom surface of the inside chamber. Subsequently, the metallic holder slides along the outside surface of the heater, and is soon fixed to the sensor element. Hence, the shift distance of the metallic holder is substantially the same as a later-described fixing portion of the metallic holder which is small. This is advantageous in that the overhang of the heater protruding upward from the open end can be suppressed to a shorter value and therefore the overall size of an air-fuel ratio sensor can be reduced.

Furthermore, in the same manner as the above-described first aspect assembling method, the tip end of the heater can be surely brought into contact with the bottom surface of the inside chamber of the sensor element. The sensor element and the heater can be surely prevented from being damaged during their assembly.

Moreover, as long as the relationship $a \geq b$ is established between the above-described clearance "a" and the shift distance "b", the tip end of the sensor element is surely prevented from accidentally colliding with the bottom surface of the inside chamber.

It is preferable that the clearance "a" is as short as possible.

Still further, it is preferable in the above-described first or second aspect assembling method that the heater is supported by a fixing jig in an upright position so that the tip end of the heater points upward, then the heater is inserted into the inside chamber of the sensor element, then the metallic holder is shifted and fixed to the sensor element, and then the fixing jig is removed from the heater.

This assembling method is suitable for an automatic assembling operation using a machine. Hence, the efficiency in the assembling operation can be improved. Especially, it is preferable that a lead wire is attached beforehand on the heater before executing the assembling operation.

In the above-described assembling method, it is possible to support the heater in an upright position so that its tip end points upward and then the sensor element is lowered from the top to assemble it with the heater. In this case, it is possible to shift the heater upward while holding the sensor element stationary.

Even further, it is preferable in the above-described first or second aspect assembling method that the metallic holder is elastically fixed to an inside surface or an outside surface of the sensor element.

In the case where the metallic holder is installed on the inside surface of the sensor element, the heater is surely prevented from being accidentally pulled out from the inside chamber, for example, by hooking the metallic holder by the jig etc.

On the other hand, in the case where the metallic holder is installed on the outside surface of the sensor element, it is surely prevented that the open end of the sensor element is closed by the metallic holder. This is advantageous in that a great amount of referential gas can be introduced into the inside chamber. Accordingly, the characteristics of the sensor element can be stabilized. Furthermore, easy introduction of the referential gas will realize a significant amount of reduction of the inside chamber volume.

Next, a third aspect of the present invention provides an assembling method for a heater-equipped air-fuel ratio sensor which comprises a cylindrical sensor element having an open end and an opposed closed end with an inside chamber defined therein and a stick-like heater inserted in the inside chamber of the sensor element so that a tip end of the heater is brought into contact with a bottom surface of the inside chamber, and the sensor element and an insulator are secured to a housing, and furthermore the heater is supported to the sensor element by a metallic holder.

More specifically, the third aspect assembling method comprises the steps of inserting the heater into the inside chamber of the sensor element until the tip end of the heater is brought into contact with the bottom surface of the inside chamber, and sliding the metallic holder along an outside surface of the heater until the metallic holder is engaged with the insulator.

In general, the sensor element is weak. The outside and inside surfaces of the sensor element are provided with electrodes and lead portions conductive with these electrodes. Both of these electrodes and lead portions are made of thin metallic films, such as Pt films, which are not strong.

In this respect, fixing the metallic holder to the insulator makes it possible to prevent the sensor element from being broken and to prevent the electrodes and lead portions from being damaged. Furthermore, as the metallic holder is installed on the rigid insulator, the fixing force of the metallic holder is enlarged and the installation is ensured.

In the same manner as the above-described first aspect assembling method, according to the above-described third aspect invention, it becomes possible to provide a method for assembling a heater-equipped air-fuel ratio sensor which is capable of surely bringing the tip end of the heater into contact with the bottom surface of the inside chamber of the sensor element, without damaging the sensor element and the heater during their assembly.

Next, it is possible to install the metallic holder to the insulator at a portion lower or more inward the upper end region thereof. In this case, the upper end region of the insulator includes both of inside and outside surfaces of the insulator as well as the top surface of the insulator.

Even further, it is preferable to provide a tapered portion or a shoulder portion somewhere in the upper end region or on the wall of the insulator for supporting the metallic holder.

According to the features of the preferred embodiments of the present invention, it is preferable that the above-described third aspect assembling method further comprise a step of installing the metallic holder elastically on an upper portion of the heater after the heater is inserted into the inside chamber of the sensor element. This is advantageous in that the assembling operation can be performed under the condition where the tip end of the heater is surely settled on the bottom surface of the inside chamber.

Alternatively, it is preferable that the above-described third aspect assembling method further comprise a step of installing the metallic holder elastically on an upper portion of the heater in advance before the heater is inserted into the inside chamber of the sensor element. This is advantageous in that the assembling operation can be simplified, and the possibility of damaging the sensor element during assembly operation can be eliminated.

Next, a fourth aspect of the present invention provides an assembling method for assembling a heater-equipped air-fuel ratio sensor which comprises a cylindrical sensor element having an open end and an opposed closed end with an inside chamber defined therein and a stick-like heater inserted in the inside chamber of the sensor element so that a tip end of the heater is brought into contact with a bottom surface of the inside chamber, and the sensor element and an insulator are secured to a housing, and furthermore the heater is supported to the sensor element by a metallic holder.

More specifically, the fourth aspect assembling method comprises the steps of installing the metallic holder elastically on an upper portion of the heater, inserting the heater into the inside chamber of the sensor element until the metallic holder is brought into contact with the insulator under a condition where the tip end of the heater is not brought into contact with the bottom surface of the inside chamber, shifting the metallic holder toward the bottom surface of the inside chamber so that the heater held by the metallic holder is further inserted in the inside chamber and the tip end of the heater is brought into contact with the bottom surface of the inside chamber of the sensor element, and sliding the metallic holder along an outside surface of the heater toward the bottom surface of the inside chamber until the metallic holder is engaged with the insulator.

In this case, the following relationship is established $$a<b$$

where "a" represents an axial clearance between the tip end of the heater and the bottom surface of the inside chamber at a moment the metallic holder is brought into contact with the insulator, while "b" represents an axial shift distance of the metallic holder with respect to the outside surface of the heater.

According to the above-described fourth aspect assembling method, the metallic holder is fixed to the insulator. Hence, it becomes possible to prevent the sensor element from being broken and also to prevent the electrodes and lead portions from being damaged. Furthermore, as the metallic holder is installed on the rigid insulator, the fixing force of the metallic holder is enlarged and the installation is ensured.

Moreover, the shift distance of the metallic holder is the same as the later-described fixing portion of the metallic holder which is significantly small. This is advantageous in that the overall size of an air-fuel ratio sensor can be reduced.

Furthermore, in the same manner as the above-described first aspect assembling method, the tip end of the heater can be surely brought into contact with the bottom surface of the inside chamber of the sensor element. The sensor element and the heater can be surely prevented from being damaged during their assembly.

Moreover, as long as the relationship $a \geq b$ is established between the above-described clearance "a" and the shift distance "b", it is the tip end of the sensor element is surely prevent from colliding accidentally or interfering with the bottom surface of the inside chamber.

It be preferable that the clearance "a" is as short as possible.

Still further, it is preferable in the above-described third or fourth aspect assembling method that the heater is supported by a fixing jig in an upright position so that the tip end of the heater points upward, then the heater is inserted into the inside chamber of the sensor element, then the metallic holder is shifted and fixed to the insulator, and then the fixing jig is removed from the heater.

This assembling method is suitable for an automatic assembling operation using a machine. Hence, the efficiency in the assembling operation can be improved. Especially, it is preferable that a lead wire is attached beforehand on the heater before executing the assembling operation.

In the above-described assembling method, it is possible to support the heater in an upright position so that its tip end points upward and then the sensor element is lowered from the top to assemble it with the heater. In this case, it is possible to shift the heater upward while holding the sensor element stationary.

Even further, it is preferable in the above-described third or fourth aspect assembling method that the metallic holder be elastically fixed to an inside surface or an outside surface of the insulator.

In the case where the metallic holder is installed on the inside surface of the insulator, the heater is surely prevented from being accidentally pulled out from the inside chamber, for example, by hooking the metallic holder by the jig etc.

On the other hand, in the case where the metallic holder is installed on the outside surface of the insulator, the open end of the sensor element is a closed by the metallic holder. This is advantageous in that a great amount of referential gas can be introduced into the inside chamber. Accordingly, the characteristics of the sensor element can be stabilized. Furthermore, easy introduction of the referential gas will realize a significant amount of reduction of the inside chamber volume.

Furthermore, according to the features of the preferred embodiments of the present invention, it is preferable in the above-described first to fourth assembling methods that the metallic holder comprise a heater holding portion elastically supporting the heater, and a fixing portion elastically engaged with an inside surface of the sensor element or an inside surface of the insulator.

This arrangement is advantageous in that the metallic holder can be easily inserted into the inside chamber. Furthermore, as an elastic force is generated in the radial direction at the fixing portion, it becomes possible to fix the metallic holder surely to the sensor element. Moreover, the configurations of the heater holding portion and the fixing portion can be variously changed. For example, the fixing portion can be formed into a cylindrical or ring shape with a cutout extending along its axial direction. Such metallic holders are fabricated by bending a thin heat-resistive metal plate.

Still further, according to the features of the preferred embodiments of the present invention, it is preferable in the above-described first to fourth assembling methods that the metallic holder comprise a heater holding portion elastically supporting the heater, and a fixing portion elastically engaged with an outside surface of the sensor element or an outside surface of the insulator.

In this case, a force acting on the sensor element or the insulator is directed radially inward. Hence, this force acts as a compression force. Both of the sensor element and the insulator are made of ceramic which is strong against compression. Accordingly, it becomes possible to prevent both of the sensor element and the insulator from being damaged. As described above, the configurations of the heater holding portion and the fixing portion can be variously changed. And, the metallic holders are fabricated by bending a thin heat-resistive metal plate.

Even further, according to the features of the preferred embodiments of the present invention, it is preferable in the above-described first to fourth assembling methods that the sensor element is assembled beforehand in a housing in a subassembly condition.

With this arrangement, it becomes possible to reduce the number of assembling processes required after assembling the heater. Accordingly, it becomes possible to prevent any interference occurring in the vicinity of the portion where the heater is installed, eliminating the possibility of causing problems.

Furthermore, it is preferable to subassemble the sensor element and the insulator beforehand in the housing. With this arrangement, it becomes possible to easily and stably install the heater in the sensor element. This is advantageous to prevent the heater from being broken.

Furthermore, according to the features of the preferred embodiments of the present invention, it is preferable in the above-described first to fourth assembling methods that the metallic holder holds the heater at a single point.

As the heater abuts the bottom surface of the inside chamber, a force supporting the heater is generated from this abutting point. If the metallic holder holds the heater at a plurality of points, a force bending the heater will be generated. Therefore, to prevent the heater from being damaged, it is preferable that the number of supporting points of the heater is only one point.

Moreover, according to the features of the preferred embodiments of the present invention, it is preferable in the above-described first to fourth assembling methods that a lead wire be installed on the heater before the heater is inserted into the inside chamber of the sensor element. This is advantageous in that the installation of the lead wire onto the heater can be simplified.

Still further, according to the features of the preferred embodiments of the present invention, it is preferable in the above-described first to fourth assembling methods that the heater has a cavity at least on its tip end. Provision of such a cavity makes it possible to prevent the center of the tip end of the heater from colliding with the bottom of the inside chamber when the heater is brought into contact with the bottom surface of the inside chamber.

In general, a reaction force acting from the bottom of the inside chamber to the tip end of the heater is increased as the abutting point therebetween approaches the center of the bottom surface. Therefore, the sensor element can be prevented from being broken by providing the cavity on the tip end of the heater.

Even further, according to the features of the preferred embodiments of the present invention, it is preferable in the above-described first to fourth assembling methods that the heater have a groove axially extending on its outside surface. With this arrangement, when the heater is inserted in the sensor element, the referential gas can be sufficiently introduced into the innermost end of the inside chamber via the axially extending groove. Accordingly, the characteristics of the sensor element can be stabilized.

Moreover, according to the features of the preferred embodiments of the present invention, the heater can be formed into a polygonal shape. In this case, it is preferable that the corners of the polygonal heater abutting the metallic holder are chamfered or cut in a curved surface. It is recommendable that a ceramic spacer is interposed between the heater and the bottom surface of the inside chamber of the sensor element. And also, it is desirable that a guide plate is disposed beforehand at the open end of the sensor element to guide the metallic holder.

BRIEF DESCRIPTION OF THE DRAWINGS

The above and other objects, features and advantages of the present invention will become more apparent from the following detailed description which is to be read in conjunction with the accompanying drawings, in which:

FIG. 1A is a vertical cross-sectional view showing a sensor element of an air-fuel ratio sensor in accordance with a first embodiment of the present invention;

FIG. 1B is a front view showing a heater of the air-fuel ratio sensor in accordance with the first embodiment of the present invention;

FIG. 5A is a front view showing a metallic holder installed on the outside surface of the heater in accordance with the first embodiment of the present invention;

FIG. 5B is a developed plan view showing a metal plate to be fabricated into the metallic holder shown in FIG. 5A;

FIG. 6 is a cross-sectional view showing an essential arrangement of a heater-equipped air-fuel ratio sensor in accordance with the first embodiment of the present invention;

FIG. 7 is a cross-sectional view showing an essential arrangement of another heater-equipped air-fuel ratio sensor in accordance with the first embodiment of the present invention;

FIG. 8 is a cross-sectional view showing an essential arrangement of still another heater-equipped air-fuel ratio sensor in accordance with the first embodiment of the present invention;

FIG. 9A is a front view showing a metallic holder installed o n the outside surface of the heater in accordance with a second embodiment of the present invention;

FIG. 9B is a developed plan view showing a metal plate to be fabricated into the metallic holder shown in FIG. 9A;

FIG. 10A is a front view showing another metallic holder installed on the outside surface of the heater in accordance with the second embodiment of the present invention;

FIG. 10B is a developed plan view showing a metal plate to be fabricated into the metallic holder shown in FIG. 10A;

FIGS. 14A through 14D are sequential views illustrating an assembling method for installing a heater into a sensor element in accordance with a third embodiment of the present invention;

FIG. 15 is a view showing a heater equipped with a lead wire and a metallic holder in accordance with the above-described first to fifth embodiments of the present invention;

FIGS. 16A and 16B are views showing an assembling method for installing a heater into a sensor element in accordance with a fourth embodiment of the present invention;

FIG. 20A is a cross-sectional view showing an essential arrangement of a sensor element installed in a housing in a subassembly condition in accordance with the sixth embodiment of the present invention;

FIG. 20B is a view showing a heater assembled with the sensor element shown in FIG. 20A;

FIG. 21 is a cross-sectional view showing an assembled condition where the heater shown in FIG. 20B is inserted into sensor element shown in FIG. 20A;

FIG. 22A is a cross-sectional view showing an essential arrangement of a sensor element installed in a housing in a subassembly condition in accordance with a seventh embodiment of the present invention;

FIG. 22B is a cross-sectional plan view showing an essential arrangement of an insulator shown in FIG. 22A;

FIG. 23 is a front view showing a heater to be assembled with the sensor element shown in FIG. 22A;

FIG. 24 is a cross-sectional view showing an essential arrangement of the heater-equipped air-fuel ratio sensor in accordance with the seventh embodiment of the present invention;

FIG. 25A is a cross-sectional view showing an essential arrangement of a sensor element installed in a housing in a subassembly condition in accordance with the seventh embodiment of the present invention;

FIG. 25B is a front view showing a heater to be assembled with the sensor element shown in FIG. 25A;

DETAILED DESCRIPTION OF THE PREFERRED EMBODIMENTS

Figure 2:
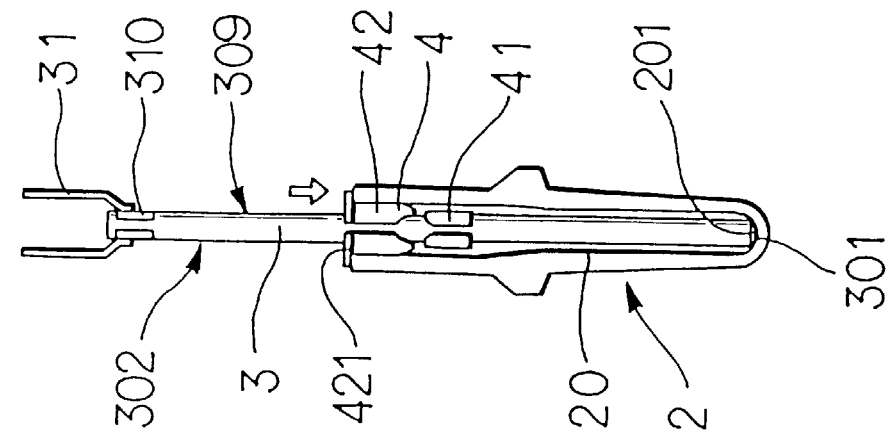
FIGS. 2, 3 and 4 are views illustrating a method for assembling the air-fuel ratio sensor in accordance with the first embodiment of the present invention.

Hereinafter, preferred embodiments of the present invention will be explained with reference to the accompanying drawings. Identical or corresponding parts are denoted by the same numerals throughout the various views.

First Embodiment

A method for assembling an air-fuel ratio sensor in accordance with a first embodiment of the present invention will be explained with reference to FIGS. 1A through 8.

As shown in FIG. 6, an air-fuel ratio sensor 1 of the present invention comprises a sensor element 2 which is configured into a cylindrical body having one end (i.e. lower end) closed and the other end (i.e. upper end) opened. This cylindrical body has a bore extending in an axial direction thereof for defining an inside chamber 20. A stick-like electric heater 3 is inserted into the inside chamber 20. A tip end 301 of heater 3 is brought into contact with or settled on a bottom surface 201 of inside chamber 20. Heater 3 itself is supported by a metallic holder 4 and fixed at a predetermined position in the sensor element 2.

FIGS. 1A and 1B respectively show the conditions of sensor element 2 and heater 3 before they are assembled. In assembling these sensor element 2 and heater 3, as shown in FIG. 2, the tip end 301 of heater 3 is inserted into the inside chamber 20 from the open end thereof until the tip end 301 reaches the bottom surface 201 of inside chamber 20.

Figure 3:
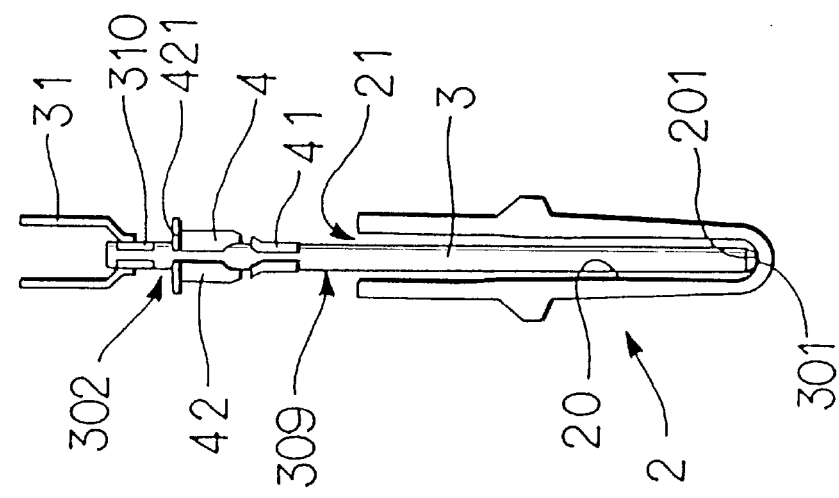

Next, as shown in FIG. 3, metallic holder 4 is elastically attached on an upper portion of heater 3. This metallic holder 4 is used to fix heater 3 to sensor element 2.

Figure 4:
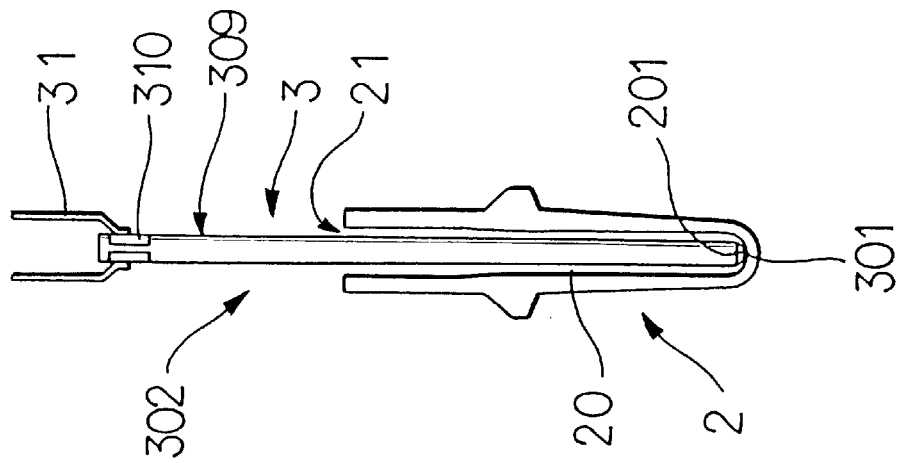

Then, as shown in FIG. 4, metallic holder 4 is shifted toward an open end 21 of sensor element 2. Metallic holder 4 slides along an outside surface 309 of heater 3, and is fixed to the open end 21 of sensor element 2.

Details of sensor element 2 will be explained hereinafter. As shown in FIG. 1A, sensor element 2 comprises a solid electrolyte 29 made of an oxygen-ion conductive material, a pair of outside and inside electrodes provided on an outside surface 209 and an inside surface 208 of this solid electrolyte 29. Furthermore, sensor element 2 has a flange portion 291 protruding radially outward from its outside surface 209.

Next, heater 3 will be explained. As shown in FIG. 1B, heater 3 is a ceramic heater accommodating inside thereof a heating element which generates heat when electric current is supplied. Heater leads 31, electrically connected to heater 3 to supply electric current, are taken out from an upper portion 302 of heater 3. Reference numeral 310 denotes a terminal portion of connecting heater leads 31 to the heater body.

Next, metallic holder 4 will be explained.

As shown in FIG. 5A, metallic holder 4 comprises a heater holding portion 41 supporting the body of heater 3, a fixing portion 42 engaged with sensor element 2, and a flange portion 421 provided integrally at an upper end of fixing portion 42 so as to protrude radially outward.

The heater holding portion 41 and fixing portion 42 are respectively configured into a cylindrical or ring shape with a cutout extending along its axial direction and integrally connected with each other through a neck portion 40. FIG. 5B shows a flat or developed metallic plate before it is fabricated into cylindrical metallic holder 4 through a bending operation.

Hereinafter, air-fuel ratio sensor 1 of the first embodiment will be explained in greater detail. As shown in FIG. 6, the air-fuel ratio sensor 1 of the first embodiment comprises a housing 10 fixedly holding sensor element 2, an element-protecting cover 13 secured to the lower end of housing 10 for protecting the lower end of sensor element 2 and defining a gas chamber 130 for storing gas to be sensed, and an atmospheric-side cover 14 secured to the upper end of housing 10 through a metallic ring 125. Numerous gas holes 131 are opened on the side surface of element-protecting cover 13.

An intermediate portion of sensor element 2 is supported through a washer 121 by a taper portion 101 formed on the inside wall of housing 10. In a space defined between a flange portion 291 of sensor element 2 and the inside wall of housing 10, there are talc 122, pad 123 and insulator 124. The lower end of atmospheric-side cover 14 is brought into contact with insulator 124. Reference numeral 292 denotes an output terminal of sensor element 2.

Next, the assembling method for assembling air-fuel ratio sensor 1 in accordance with the first embodiment will be explained in greater detail.

First of all, as shown in FIGS. 1A and 1B, a pair of sensor element 2 and heater 3 are prepared. Next, heater 3 is inserted into inside chamber 20 of sensor element 2. Then, tip end 301 of heater 3 is brought into contact with or settled on the bottom surface 201 of inside chamber 20. Next, as shown in FIG. 3, metallic holder 4 is attached to the body of heater 3 at the upper portion 302 of heater 3 beneath the terminal portion 310.

Next, as shown in FIG. 4, metallic holder 4 is shifted downward to slide along the outside surface 309 of heater 3. The fixing portion 42 of metallic holder 4 is housed in the upper part of inside chamber 20, and flange portion 421 is engaged with the open end 21 of inside chamber 20.

The fixing portion 42 causes an elastic force acting in the radial direction of inside chamber 20. Urged by this elastic force, the metallic holder 4 is resiliently fixed to the wall of inside chamber 20 in the vicinity of open end 21. With this arrangement, heater 3 is surely fixed to sensor element 2.

Then, heat leads 31 of heater 3 and output terminal 292 of sensor element 2 are connected to lead wires. Through these lead wires, electric current is supplied to heater 3 and an output of sensor element 2 is taken out.

Next, as shown in FIG. 6, the sensor element 2 assembled with heater 3 is disposed in a predetermined position in the housing 10 through a ring washer 121. Then, talc 122, pad 123 and insulator 124 are successively accumulated on the flange portion 291 of sensor element 2. Meanwhile, element-protecting cover 13 is attached in advance to the lower end of housing 10. Then, the atmospheric-side cover 14 is attached through metallic ring 125 to the housing 10. Other components (not shown) are installed too.

The assembling process or procedure, other than the assembling of the heater 3 into the inside chamber 20 of sensor element 2, is not limited to the above-described one and can be modified flexibly.

Next, function and effect of the above-described first embodiment will be explained.

According to the assembling method of the first embodiment of the present invention, stick-like heater 3 is inserted in the inside chamber 20 until its tip end 301 is brought into contact with or settled on the bottom surface 201 of the inside chamber 20, and then metallic holder 4 is installed on the heater 3.

With this arrangement, when the heater 3 is inserted into the inside chamber 20, it becomes possible to bring heater 3 into contact with the bottom surface 201 of inside chamber 20 safely without causing part of heater 3 to collide or interfere with other components constituting air-fuel ratio sensor 1. In other words, the heater 3 can be smoothly inserted in the inside chamber 20 and surely brought into contact with or settled on the bottom surface 201.

Subsequently, under the condition where the heater 3 keeps contact with the bottom surface 201 of inside chamber 20, metallic holder 4 is elastically attached to the upper portion 302 on the outside surface 309 of heater 3. Then, a force acting toward the open end 21 of inside chamber 20 is applied on the metallic holder 4. Impelled by this force, the metallic holder 4 slides along the outside surface 309 of heater 3 and reaches the open end 21 of inside chamber 20.

The metallic holder 4, as having elasticity as described above, can be resiliently engaged and fixed to the open end 21 of inside chamber 20.

Furthermore, when the metallic holder 4 slides along the outside surface 309 of heater 3, a sliding frictional force is caused between heater holding portion 41 and the outside surface 309 of heater 3. With this sliding frictional force, the heater 3 can be firmly pressed to the bottom surface 201 of inside chamber 20. The contact between tip end 301 and bottom surface 201 is maintained until metallic holder 4 is fixed to the open end 21. Accordingly, the tip end 301 of heater 3 is surely fixed while keeping contact with the bottom surface 201 of inside chamber 20.

As described above, a force acting on the bottom surface 201 of sensor element 2 is substantially equivalent to a pressing force acting in the axial direction by the above-described sliding frictional force. Thus, heater 3 can be fixed in the inside chamber 20 with its tip end 301 kept in firm contact with bottom surface 201 of inside chamber 20 without adding an excessive force to sensor element 2. Furthermore, sensor element 2 and heater 3 can be surely prevented from being damaged during their installation.

According to the first embodiment, the metallic holder 4 is used to fix heater 3 to the open end 21. However, as shown in FIG. 7, it is possible to fix metallic holder 4 to the outside surface 209 of sensor element 2.

With this arrangement, it becomes possible to prevent the metallic holder 4 from closing open end 21. Thus, a greater amount of referential gas can be introduced into inside chamber 20 from open end 21. Thus, the characteristics of sensor element 2 can be stabilized.

According to the first embodiment, the inside chamber 20 of sensor element 2 has flush inside surface 208. However, as shown in FIG. 8, it is possible to provide a shoulder portion (or a tapered portion) 205 on the inside surface 208 in the vicinity of open end 21, so that the metallic holder 4 can be supported by this shoulder portion 205. In this case, flange portion 421 of metallic holder 4 shown in FIG. 4 can be omitted.

Second Embodiment

A second embodiment chiefly discloses various types of the metallic holder used in the assembling method for an air-fuel ratio sensor in accordance with the present invention as shown in FIGS. 9A through 13B.

More specifically, a metallic holder 5 shown in FIG. 9A will be explained. Metallic holder 5 comprises a cylindrical body 50, a total of three spring pieces 59 spaced mutually in a circumferential direction and each extending downward from cylindrical body 50, and a total of four flanges 501 provided at the upper end of cylindrical body 50 so as to protrude radially outward.

Each spring piece 59 is bent substantially in a V shape. A bent portion 51, located at the center of spring piece 59 and protruding radially inward, serves as a heater supporting portion holding heater 3. Meanwhile, another bent portion 52, provided at the lower end of spring piece 59 and protruding radially outward, serves as a fixing portion engaged or coupled with the open end 21 of sensor element 2. It is, of course, possible to form cylindrical body 50 into a configuration engageable with the sensor element 2 so as to act as a fixing portion to the sensor element 2.

FIG. 9B shows a flat or developed metallic plate before it is fabricated into the above-described cylindrical metallic holder 5 through a bending operation. Other arrangement of this example is substantially the same as that of the first embodiment.

According to the configuration of the above-described metallic holder 5, the portion of metallic holder 5 directly brought into contact with the outside surface 309 of heater 3 can be minimized to a line- or point-like small region. This is advantageous in that the metallic holder 5 can slide easily. Furthermore, effects of the above-described first embodiment can be obtained similarly.

Next, a metallic holder 4 shown in FIG. 10A will be explained. This metallic holder 4, which is slightly modified from the metallic holder 4 shown in FIG. 5A, comprises a fixing portion 42 engaged with sensor element 2, two flange portions 421 provided integrally at an upper end of fixing portion 42 so as to protrude radially outward, and a pair of upper and lower heater holding portions 41 integrally connected to the fixing portion 42 via neck portions 40. These heater holding portions 41 and fixing portion 42 are respectively configured into a cylindrical or ring shape with a cutout extending along its axial direction. FIG. 10B shows a flat or developed metallic plate before it is fabricated into the above-described cylindrical metallic holder 4 of FIG. 10A through a bending operation. Other arrangement of this example is substantially the same as that of the first embodiment. Furthermore, effects of the first embodiment are obtained similarly.

When compared with the metallic holder 4 having two heater holding portions 41 shown in FIG. 10A, providing only one heater holding portion 41 to metallic holder 4 as shown in FIG. 5A is preferable. Supporting heater 3 at a total of three portions as shown in FIG. 10A is relatively weak against deflection of heater 3 and sensor element 2 or distortion of metallic holder 4, and there is a tendency that a three-point bending moment is caused. In this respect, the metallic holder 4 shown in FIG. 5A is superior to the metallic holder 4 shown in FIG. 10A.

Next, a metallic holder 4 shown in FIG. 11A will be explained. This metallic holder 4, which is slightly modified from the metallic holder 4 shown in FIG. 5A or FIG. 10A, comprises a heater holding portion 41 supporting the body of heater 3, a fixing portion 42 provided under the heater holding portion 41 and engaged with sensor element 2, and a flange portion 421 provided integrally at a lower end of the fixing portion 42 so as to protrude radially outward. These heater holding portion 41 and fixing portion 42 are respectively configured into a cylindrical or ring shape with a cutout extending along its axial direction and integrally connected with each other via a neck portion 40. FIG. 11B shows a flat or developed metallic plate before it is fabricated into the above-described cylindrical metallic holder 4 of FIG. 11A through a bending operation. Other arrangement of this example is substantially the same as that of the first embodiment.

Figure 11A:
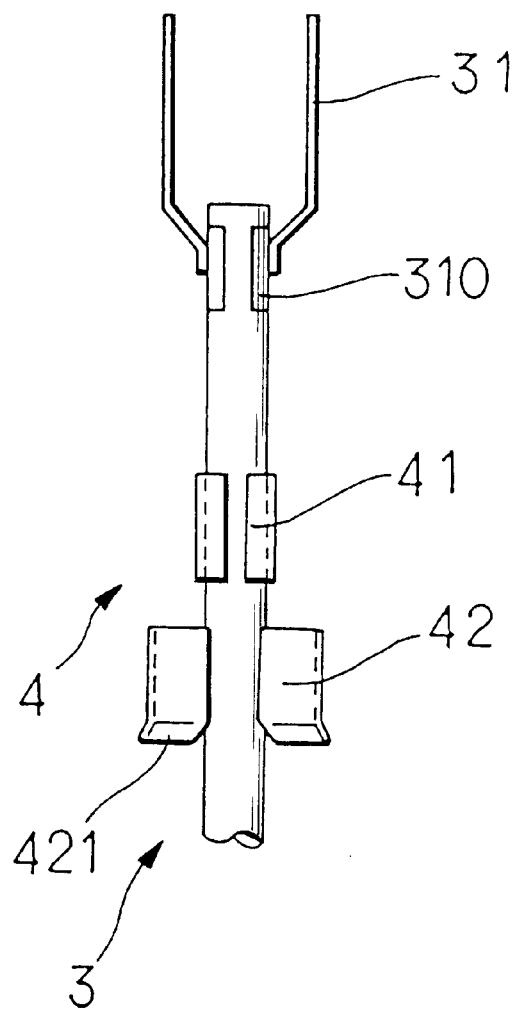
FIG. 11A is a front view showing still another metallic holder installed on the outside surface of the heater in accordance with the second embodiment of the present invention.
Figure 11B:
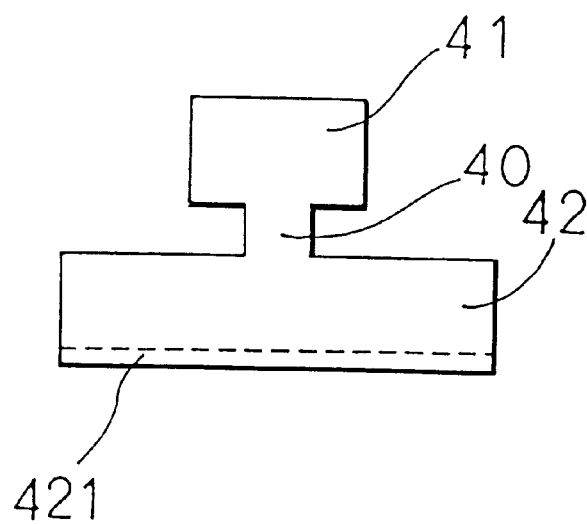
FIG. 11B is a developed plan view showing a metal plate to be fabricated into the metallic holder shown in FIG. 11A.

According to the configuration of metallic holder 4 shown in FIG. 11A, the metallic holder 4 is engaged from the outside to an outside surface of the sensor element 2 in the proximity of its open end 21. This is advantageous in that the open end 21 is surely prevented from being damaged. Furthermore, effects of the first embodiment are obtained similarly.

Next, a metallic holder 4 shown in FIG. 12A will be explained. This metallic holder 4, which is slightly modified from the metallic holder 4 shown in FIG. 5A, comprises a heater holding portion 41 supporting the body of heater 3, a fixing portion 42 provided above the heater holding portion 41 and engaged with sensor element 2, and a flange portion 421 provided integrally at an upper end of fixing portion 42 so as to protrude radially outward. These heater holding portion 41 and fixing portion 42 are respectively configured into a cylindrical or ring shape with a cutout extending thoroughly along its axial direction and integrally connected with each other via a neck portion 40. Furthermore, there, is a lead piece 45 extending upward from the upper end of fixing portion 42. This lead piece 45 acts as a means for taking out an output from the inside electrode of sensor element 2. FIG. 12B shows a flat or developed metallic plate before it is fabricated into the above-described cylindrical metallic holder 4 of FIG. 12A through a bending operation. Other arrangement of this example is substantially the same as that of the first embodiment.

Figure 12A:
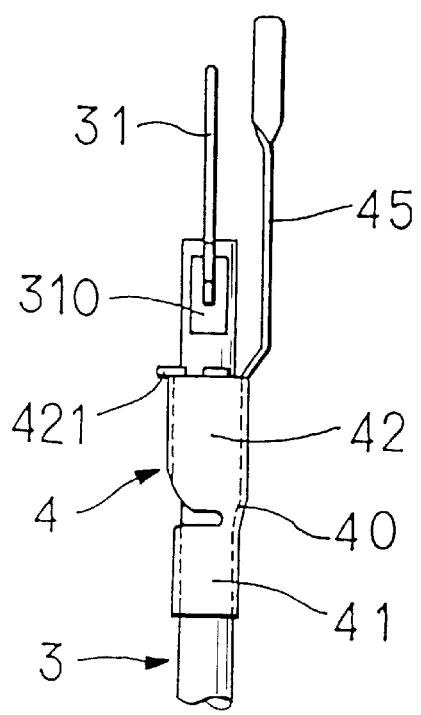
FIG. 12A is a front view showing yet another metallic holder installed on the outside surface of the heater in accordance with the second embodiment of the present invention.
Figure 12B:
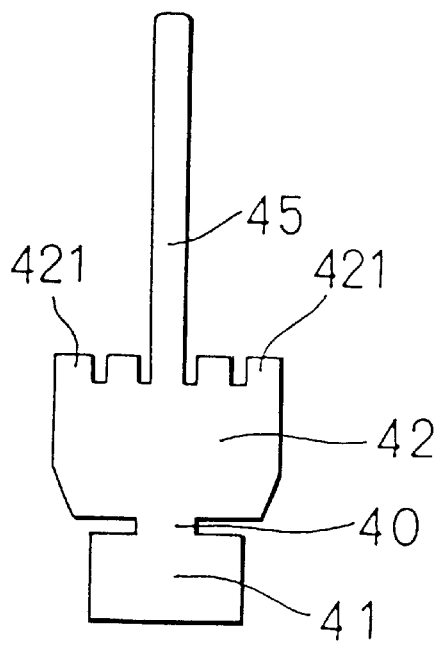
FIG. 12B is a developed plan view showing a metal plate to be fabricated into the metallic holder shown in FIG. 12A.

According to the configuration of metallic holder 4 shown in FIG. 12A, the metallic holder 4 is directly connected with the inside electrode provided in the inside chamber 20 of sensor 2 or connected to a lead portion electrically conductive with this inside electrode. With this arrangement, an output of the inside electrode can be taken out to the outside via the above-described metallic holder 4 and lead piece 45. Accordingly, there is no necessity of providing a lead piece independently or separately. Thus, the number of parts can be reduced and the assembling operation can be simplified. Furthermore, effects of the first embodiment are obtained similarly.

Figure 13A:
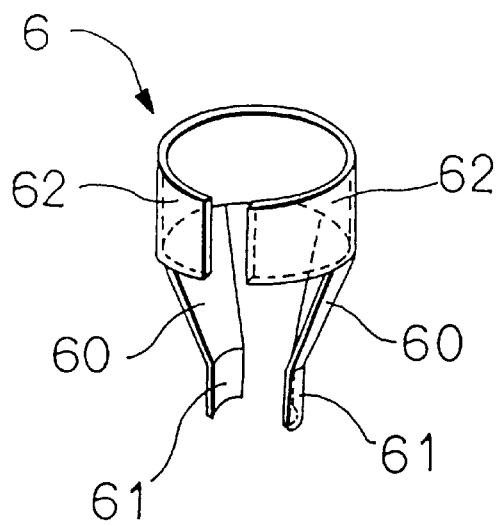
FIGS. 13A and 13B are perspective views showing other metallic holders in accordance with the second embodiment of the present invention.

Next, a metallic holder 6 shown in FIG. 13A will be explained. This metallic holder 6 comprises separated heater holding portions 61 supporting the body of heater 3, a single fixing portion 62 provided above the heater holding portions 61 and engaged with sensor element 2, and connecting portions 60 connecting the heater holding portions 61 to the fixing portion 62. Fixing portion 62 is configured into a cylindrical or ring shape with a cutout extending thoroughly along its axial direction. Two connecting portions 60, provided under the fixing portion 62, are respectively configured into a sector-like shape. Each heater holding portion 61 is integrally connected to the lower end of connecting portion 60 and configured into an arcked belt-like shape.

Figure 13B:
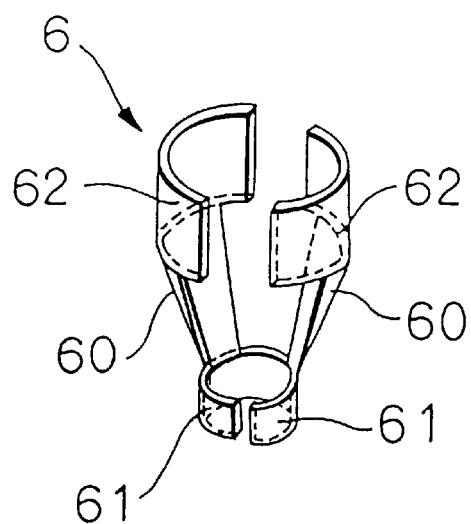

A metallic holder 6 shown in FIG. 13B will be explained. This metallic holder 6 comprises a single heater holding portion 61 supporting the body of heater 3, separated fixing portions 62 provided above the heater holding portion 61 and engaged with sensor element 2, and connecting portions 60 connecting the heater holding portion 61 to the fixing portions 62. Heater holding portion 61 is configured into a cylindrical or ring shape with a cutout extending along its axial direction. Two connecting portions 60, provided above the heater holding portion 61, are respectively configured into a sector-like shape. Each fixing portion 62 is integrally connected to the upper end of connecting portion 60 and configured into an arcked belt-like shape.

Other arrangement of this example is substantially the same as that of the first embodiment. Furthermore, effects of the first embodiment are obtained similarly.

Third Embodiment

A third embodiment chiefly discloses a method for inserting a heater 3 assembled with a metallic holder 4 into a sensor element 2, as shown in FIGS. 14A to 14D.

More specifically, as shown in FIG. 14A, sensor element 2 and heater 3 similar to the ones disclosed in the first embodiment are prepared. Next, as shown in FIG. 14B, metallic holder 4 is elastically installed on heater 3 at upper portion 302 to fix the heater 3 to sensor element 2. Configuration of the metallic holder 4 is the same as that disclosed in the first embodiment (refer to FIG. 5A).

Next, as shown in FIG. 14C, heater 3 is inserted into inside chamber 20 until tip end 301 of heater 3 is brought into contact with or settled on bottom surface 201 of inside chamber 20.

Subsequently, as shown in FIG. 14D, metallic holder 4 is slid along outside surface 309 of heater 3, so that metallic holder 4 shifts toward open end 21 of inside chamber 20 of sensor element 2. Then, the metallic holder 4 is fixed to the open end 21. After that, sensor element 2 is assembled in the housing 10 to fabricate an air-fuel ratio sensor. Others are substantially identical with those of the first embodiment.

According to the assembling method of the present invention, installation of metallic holder 4 onto heater 3 can be easily performed. Furthermore, effects of the first embodiment are obtained similarly.

In the above-described or later-described embodiments, it will be preferable to connect a joint terminal 380 and a lead wire 38 to each heater lead 31 of heater 3 in advance as shown in FIG. 15. With this arrangement, installation of lead wire 38 to heater 3 can be simplified.

Fourth Embodiment

A fourth embodiment of the present invention discloses an assembling method for assembling heater 3 to sensor element 2 in a temporarily-floating condition where tip end 301 of heater 3 is momentarily spaced from bottom surface 201 of inside chamber 20 at a moment part of metallic holder 4 holding heater 3 is first brought into contact with the upper portion of sensor element, as shown in FIG. 16A.

More specifically, sensor element 2 and heater 3 similar to the ones disclosed in the first embodiment are prepared (refer to FIG. 14A). Then, metallic holder 4 is elastically installed on heater 3 at upper portion 302 to fix the heater 3 to sensor element 2 (refer to FIG. 14B). Configuration of the metallic holder 4 is the same as that disclosed in the first embodiment (refer to FIG. 5A).

According to the fourth embodiment, when the lower end of fixing portion 42 of metallic holder 4 is first brought into contact with the open end 21 of inside chamber 20 during the inserting operation of heater 3 into inside chamber 20 of sensor 2, the tip end 301 of heater 3 is not brought into contact with the bottom surface 201 of inside chamber 20, as shown in FIG. 16A.

Subsequently, the metallic holder 4 is pushed downward so that the metallic holder 4 holding the heater 3 shifts toward the bottom surface 201 of inside chamber 20. During this downward shift movement of metallic holder 4, the tip end 301 of holder 3 is first brought into contact with the bottom surface 201 of inside chamber 20. After that, the metallic holder 4 is further pressed downward until the flange portion 421 of metallic holder 4 reaches the open end 21 of sensor element 2, as shown in FIG. 16B.

More specifically, after the condition shown in FIG. 16A, metallic holder 4 is slid along the outside surface 309 of heater 3 at its heater holding portion 41 toward the bottom surface 201 of sensor element 2 to causes a frictional slide movement with respect to the heater 3. Thus, installation of metallic holder 4 onto sensor element 2 is finished.

According to the above-described assembling method of the fourth embodiment, the following relationship needs to be established.

$$a<b$$

where "a" represents an axial clearance between the tip end of heater 3 and the bottom surface 201 (more particularly, a contact point 27) of inside chamber 20 in the condition of FIG. 16A, while "b" represents an axial shift distance of metallic holder 4 when the metallic holder 4 shifts downward from the condition of FIG. 16A to the condition of FIG. 16B. It can be also defined that "a" is an axial shift distance of heater 3 when the heater shifts downward from the condition of FIG. 16A to the condition of FIG. 16B. Others are substantially identical with those of the first embodiment.

According to the assembling method of the fourth embodiment, at the final stage of the inserting operation of heater 3 into inside chamber 20, the metallic holder 4 is brought into contact with the open end 21 at the lower end of its fixing portion 42 before the tip end 301 of heater 3 reaches the bottom surface 201 of inside chamber 20.

Thereafter, metallic holder 4 is depressed downward. As a result, the tip end 301 of heater 3 is soon brought into contact with the bottom surface 201 of inside chamber 20 of sensor element 2. After that, the metallic holder 4 is further depressed downward to continue the sliding movement along the outside surface 309 of heater 3 until the flange portion 421 of metallic holder 4 reaches the open end 21 of sensor element 2. Accordingly, the axial shift distance "b" of metallic holder 4 is substantially equal to the axial length of the fixing portion 42. This is advantageous in that the overhang of heater 3 protruding upward from open end 21 can be suppressed to a shorter value and therefore the overall size of an air-fuel ratio sensor can be reduced.

Furthermore, effects of the first embodiment are obtained similarly.

Fifth Embodiment

A fifth embodiment of the present invention discloses an assembling method for inserting heater 3 into sensor element 2 under a condition where these components are placed upside down, as shown in FIGS. 17A through 19.

More specifically, sensor element 2 and heater 3 similar to the ones disclosed in the first embodiment are prepared (refer to FIG. 14A). Metallic holder 4 is installed beforehand on heater 3 at the upper portion in the same manner as in the third embodiment.

Figure 17A:
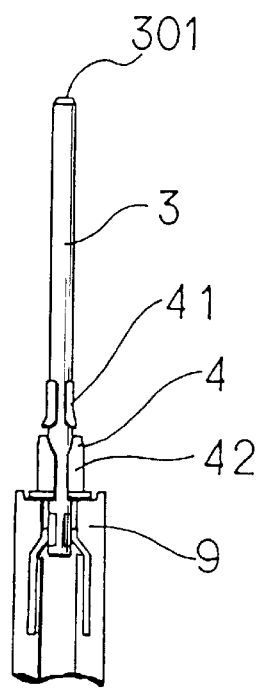
FIG. 17A is a view illustrating a heater placed upside down before installation to a sensor element in accordance with a fifth embodiment of the present invention.
Figure 17B:
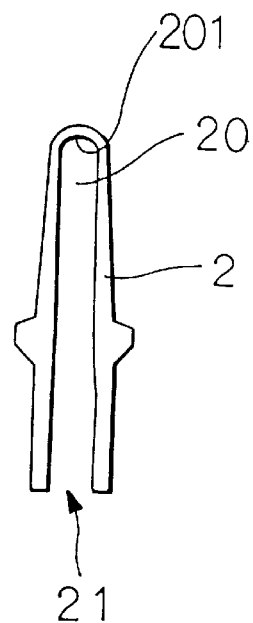
FIG. 17B is a view illustrating the sensor element to be assembled with the heater shown in FIG. 17A in accordance with the fifth embodiment of the present invention.

Next, as shown in FIG. 17A, heater 3 is fixed to a supporting jig 9 in an upright position where the tip end 301 of heater 3 points upward. Meanwhile, as shown in FIG. 17B, sensor element 2 is fixed to another supporting jig (not shown) in an upright position where its open end 21 faces downward.

Next, both heater 3 and sensor element 2 are disposed in a predetermined relationship where heater 3 and sensor element 2 are spaced in an up-and-down direction while their axes meet. Then, heater 3 is shifted toward the open end 21 of sensor element 2 and inserted in the inside chamber 20 of sensor element 2. In this condition, the tip end 301 of heater 3 is not brought into contact with the bottom surface 201 of inside chamber 20.

Figure 18:
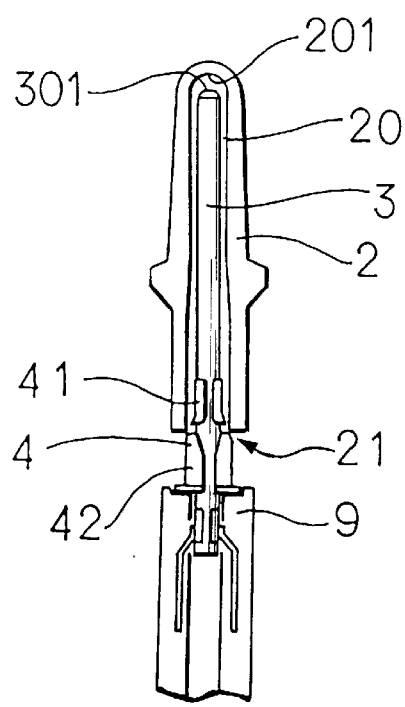
FIGS. 18 and 19 are views showing an assembling method of a heater-equipped air-fuel ratio sensor in accordance with the fifth embodiment of the present invention.
Figure 19:
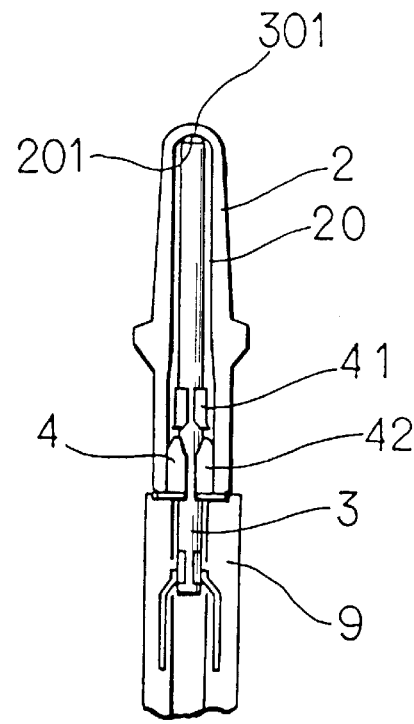

Subsequently, as shown in FIG. 18, metallic holder 4 is slid along the outside surface 309 of heater 3 until the metallic holder 4 is surely engaged with the open end 21 of inside chamber 20 (refer to FIG. 19). Then, both heater 3 and sensor element 2 are removed from their supporting jigs. Others are substantially identical with those of the first embodiment.

According to the assembling method of the fifth embodiment of the present invention, it becomes possible to support the heater 3 in the upright position by solely supporting the heater 3 from bottom by utilizing the metallic holder 4. This is advantageous in that an automatic assembling operation using a machine will be easily introduced and the efficiency of this assembling operation can be increased. Furthermore, effects of the first embodiment are obtained similarly.

Sixth Embodiment

A sixth embodiment of the present invention discloses an assembling method for assembling heater 3 to sensor element 2 under a condition where the sensor element is assembled beforehand with housing 10, as shown in FIG. 20A to FIG. 21.

More specifically, sensor element 2 and heater 3 similar to the ones disclosed in the first embodiment are prepared (refer to FIG. 14A). Metallic holder 4 is installed beforehand on heater 3 at the upper portion in the same manner as in the third embodiment, as shown in FIG. 20B.

Next, as shown in FIG. 20A, sensor element 2 is disposed in housing 10 through ring washer 121. Then, talc 122, pad 123 and insulator 124 are successively accumulated on the flange portion 291 of sensor element 2. Meanwhile, element-protecting cover 13 is attached in advance to the lower end of housing 10. Then, the atmospheric-side cover 14 is attached through metallic ring 125 to the housing 10. The upper end portion of housing 10 is caulked to fix the atmospheric-side cover 14, thereby accomplishing a subassembly. Next, heater 3 is inserted into inside chamber 20 of sensor element 2 so that the tip end 301 of heater 3 is brought into contact with the bottom surface 201 of inside chamber 20. Thereafter, metallic holder 4 is slid toward the bottom surface 201 of inside chamber 20 along the outside surface 309 of heater 3 and fixed to the open end 21 of sensor element 2. It is possible to perform the above-described assembling operation in accordance with the fourth embodiment. Others are substantially the same as those of the first embodiment.

According to the assembling method of the sixth embodiment, some of assembling processes required after assembling the heater 3 can be eliminated. Accordingly, it becomes possible to prevent any interference occurring in the vicinity of the portion where the heater 3 is installed. Furthermore, effects of the first embodiment are obtained similarly.

Seventh Embodiment

A seventh embodiment of the present invention discloses an assembling method for fixing the metallic holder to an insulator in an air-fuel ratio sensor, as shown in FIGS. 22A through 26.

More specifically, sensor element 2 and heater 3 similar to the ones disclosed in the first embodiment are prepared (refer to FIG. 14A). Metallic holder 4 is installed beforehand on heater 3 at the upper portion in the same manner as in the third embodiment, as shown in FIG. 23.

Next, as shown in FIG. 22A, sensor element 2 is disposed in housing 10 through ring washer 121. Then, talc 122, pad 123 and insulator 128 are successively accumulated on the flange portion 291 of sensor element 2. Meanwhile, element-protecting cover 13 is attached in advance to the lower end of housing 10.

As shown in FIG. 22B, insulator 128 has a cutout portion 127 providing a space for wiring an output terminal 292 of sensor element 2.

Then, the atmospheric-side cover 14 is attached through metallic ring 125 to the housing 10. The upper end portion of housing 10 is caulked to fix the atmospheric-side cover 14, thereby accomplishing a subassembly.

Next, heater 3 is inserted into inside chamber 20 of sensor element 2 so that the tip end 301 of heater 3 is brought into contact with or settled on the bottom surface 201 of inside chamber 20. Thereafter, metallic holder 4 is slid toward the insulator 128 and then engaged fixedly with an upper end 129 of insulator 128, as shown in FIG. 24.

It is possible to perform the above-described assembling operation in accordance with the first or fourth embodiment above-described. In this case, the opponent member fixedly engaging with metallic holder 4 is the insulator 128, not the sensor element 2. Others are substantially the same as those of the first embodiment.

In general, sensor element 2 is weak in its strength. The outside and inside surfaces of sensor element 2 are provided with the outside electrode and inside electrode, respectively. Both electrodes are made of thin metallic films which are not strong in the strength.

In this respect, the assembling method of the above-described seventh embodiment fixes the metallic holder 4 to insulator 128 to make it possible to prevent sensor element 2 and the electrodes from being damaged. Furthermore, as metallic holder 4 is installed on the rigid insulator 128, the fixing force of metallic holder 4 is enlarged and the installation is ensured.

Figure 26:
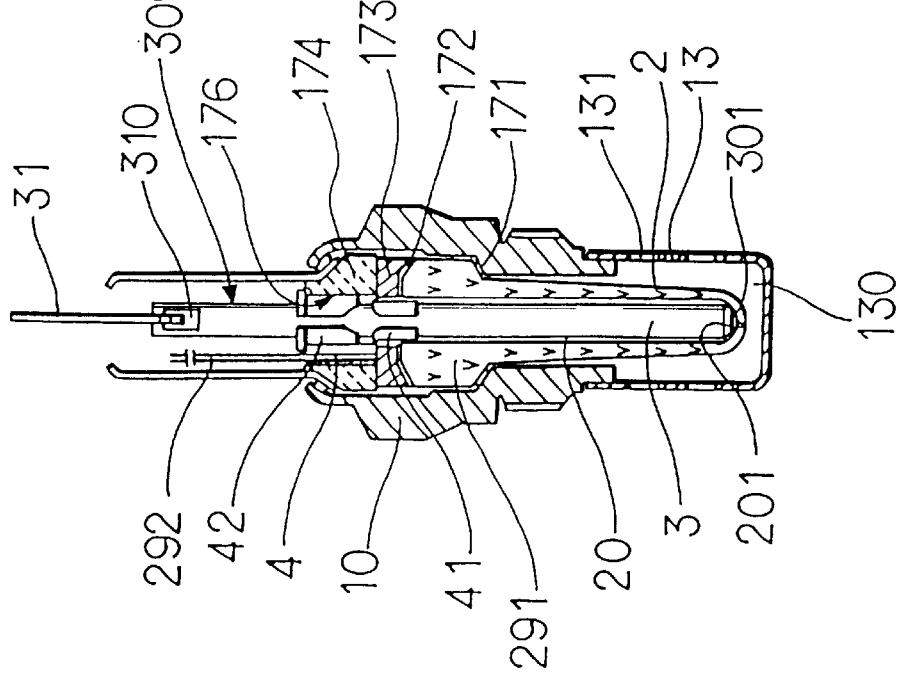
FIG. 26 is a cross-sectional view showing an essential arrangement of the heater-equipped air-fuel ratio sensor in accordance with the seventh embodiment of the present invention.

Moreover, the assembling method of the seventh embodiment can be applied to an air-fuel ratio sensor 1 shown in FIGS. 25A to 26.

The air-fuel ratio sensor 1, as shown in FIG. 26, comprises sensor element 2 disposed in housing 10 through a washer packing 171. A metallic flange 173 is disposed on the flange 291 of sensor element 2 through a packing 172. Furthermore, an insulator 174 is disposed on the metallic flange 173. Moreover, an output terminal 292 of sensor element 2 is securely welded to the metallic flange 173 to take out an electrical output from sensor element 2.

More specifically, in the assembling of the heater and sensor element of the air-fuel ratio sensor 1, sensor element 2 and heater 3 similar to the ones disclosed in the first embodiment are prepared (refer to FIG. 14A). Metallic holder 4 is installed beforehand on heater 3 at the upper portion in the same manner as in the third embodiment, as shown in FIG. 25B.

Next, as shown in FIG. 25A, sensor element 2 is assembled with housing 10 so as to accomplish a subassembly. Then, heater 3 is inserted into inside chamber 20 of sensor element 2 so that the tip end 301 of heater 3 is brought into contact with or settled on the bottom surface 201 of inside chamber 20. Thereafter, metallic holder 4 is slid toward the insulator 174 along the outside surface 309 of heater 3 and then fixedly engaged with an upper end 176 of insulator 174. Others are substantially identical with those of the first embodiment.

In the same manner as the above-described air-fuel ratio sensor, the metallic holder 4 is fixed to insulator 174 to prevent sensor element 2 and the electrodes from being damaged. Furthermore, as metallic holder 4 is installed on the rigid insulator 174, the fixing force of metallic holder 4 is enlarged and the installation is ensured. Moreover, effects of the first embodiment are obtained similarly.

Eighth Embodiment

Figure 28:
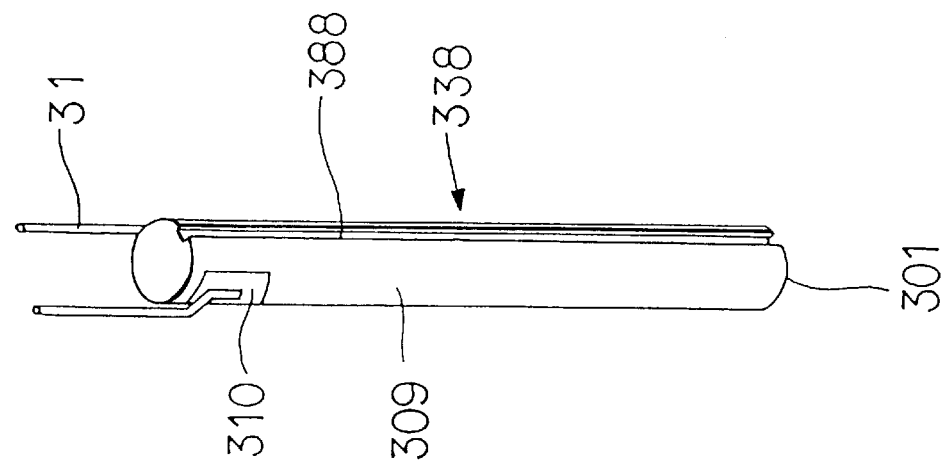
FIG. 28 is a perspective view showing a heater having an axial groove in accordance with the eighth embodiment of the present invention.
Figure 27:
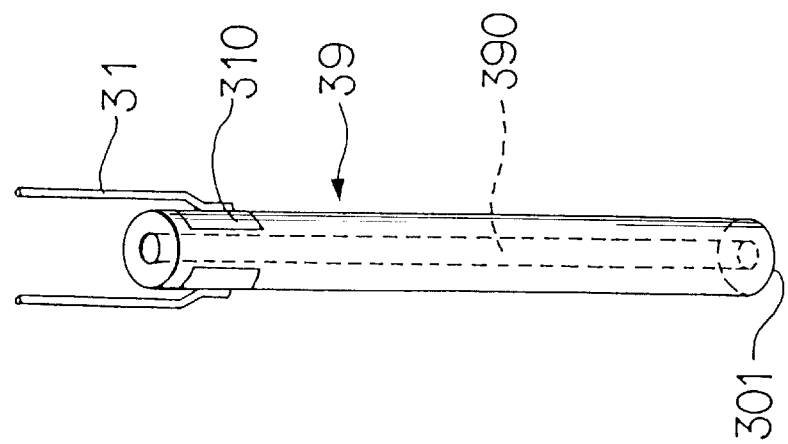
FIG. 27 is a perspective view showing a heater having an axial cavity in accordance with an eighth embodiment of the present invention.

An eighth embodiment of the present invention discloses a heater having an axial cavity as shown in FIG. 27 and a heater having an axial groove as shown in FIG. 28.

A heater 39 shown in FIG. 27 comprises a cavity 390 extending along its central axis from tip end 301 to the upper end. Other arrangement is substantially the same as that of the first embodiment.

A heater 338 shown in FIG. 28 comprises a groove 388 extending along its outside surface 309 from tip end 301 to the upper end. Other arrangement is substantially the same as that of the first embodiment.

In the assembling operation of heater 338 to sensor element 2, heater 39 is brought into contact with the bottom surface 201 of inside chamber 20. In this abutting condition, it is surely prevented that the central region of the tip end 301 of heater 39 directly contacts with the bottom surface 201. If the central region of the tip end 301 of heater 39 is configured to protrude toward the bottom surface 201 than other region of the tip end 301, there will be a possibility that the heater 39 will first collide or interfere with the bottom surface 201 at this central region. A concentrated force will act on the central region of the tip end. There is a significant possibility of damaging the bottom surface 201 of sensor element 2.

Hence, by providing cavity 390 in this central region, it becomes possible to prevent the bottom surface 201 from being damage.

Moreover, according to the heater 338 of the eighth embodiment, referential gas can be sufficiently introduced to the innermost end of inside chamber 20 via groove 388. Accordingly, the characteristics of sensor element 2 can be stabilized.

Ninth Embodiment

Figure 29:
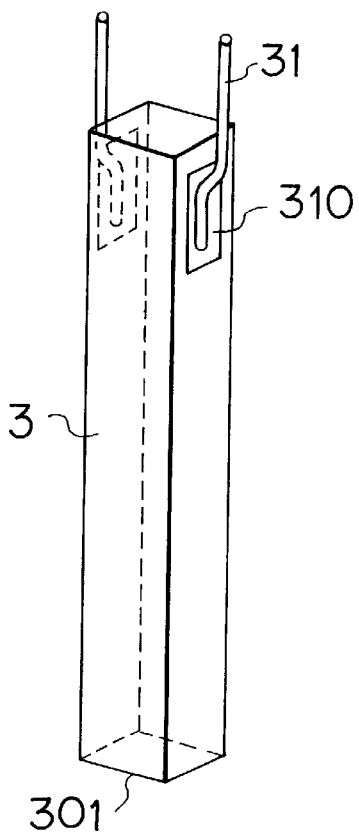
FIG. 29 is a perspective view showing a prismatic heater in accordance with a ninth embodiment of the present invention.
Figure 30A:
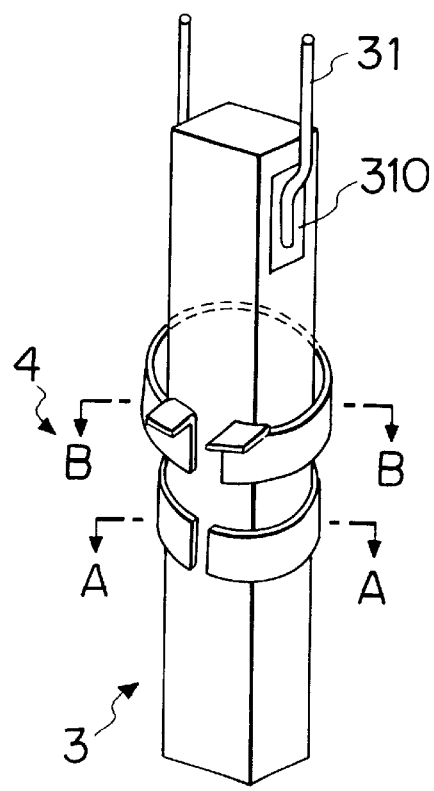
FIG. 30A is a perspective view showing a metallic holder installed on the prismatic heater in accordance with the ninth embodiment of the present invention.
Figure 30B:
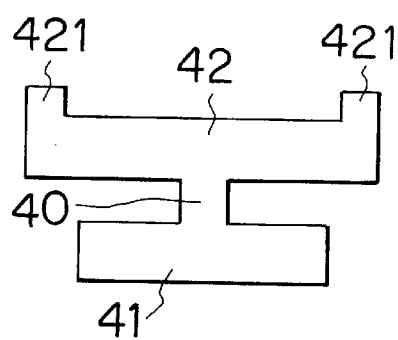
FIG. 30B is a developed plan view showing a metal plate to be fabricated into the metallic holder shown in FIG. 30A.
Figure 30C:
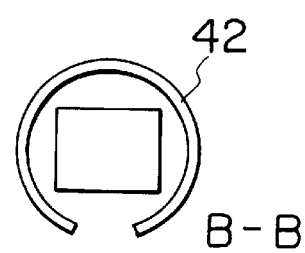
FIG. 30C is a cross-sectional view taken along a line B—B of FIG. 30A.
Figure 30D:
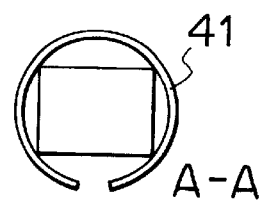
FIG. 30D is a cross-sectional view taken along a line A—A of FIG. 30A.
Figure 31A:
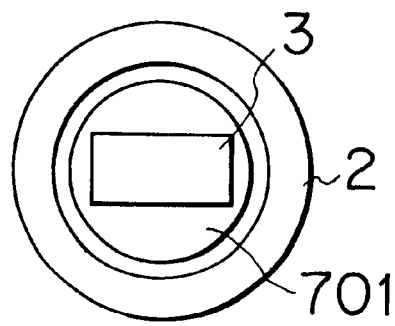
FIG. 31A is a plan view showing an assembly of a prismatic heater and a sensor element with a ceramic spacer in accordance with the ninth embodiment of the present invention.

A ninth embodiment of the present invention discloses a polygonal heater having a rectangular cross section, as shown in FIGS. 29 to 30D.

A heater 3 shown in FIG. 29 is a prismatic heater having a square cross section. FIG. 30 shows a condition where a cylindrical metallic holder 4 is installed on the heater 3. More specifically, metallic holder 4 comprises a cylindrical heater holding portion 41 supporting the body of prismatic heater 3, a cylindrical fixing portion 42 engaged with sensor element 2, and two flange portions 421 provided integrally at an upper end of fixing portion 42 so as to protrude radially outward. Heater holding portion 41 and fixing portion 42 and connected integrally by a neck portion 40.

The cylindrical heater holding portion 41 of metallic holder 4 elastically holds four corners of prismatic heater 3. In this case, it is preferable that the corners of prismatic heater 3 abutting metallic holder 4 are chamfered or cut in a curved surface to prevent each corner of heater 3 from being cracked.

Furthermore, it is preferable that the edge of tip end 301 of heater 3 is chamfered or cut in a curved surface to prevent the tip end 301 from being cracked or damaged when brought into contact with bottom surface 201 of sensor element 2.

Figure 31B:
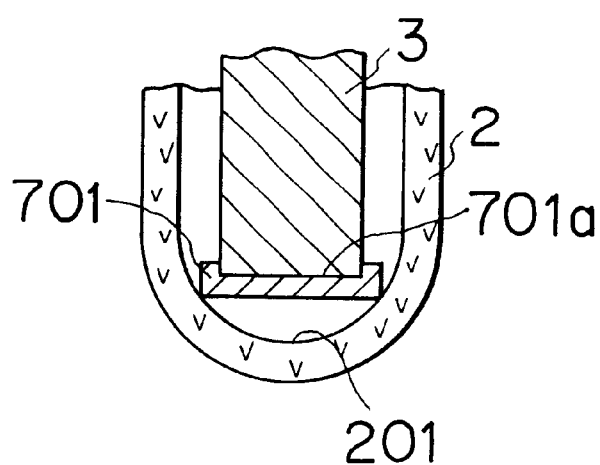
FIG. 31B is a vertical cross-sectional view showing the assembly shown in FIG. 31A.
Figure 32:
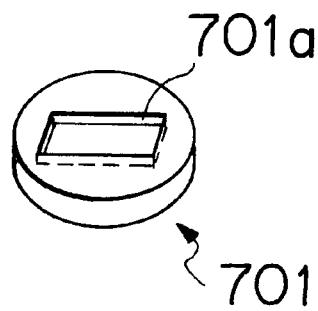
FIG. 32 is a perspective view showing one example of the spacer shown in FIG. 31B.

The configuration of the above-described ninth embodiment is strong against a bending force during the assembling operation. Furthermore, according to the above-described ninth embodiment, it is allowed to insert or interpose a ceramic spacer 701 or the like between the tip end 301 of heater 3 and the bottom surface 201 of sensor element 2, as shown in FIGS. 31B and 32. Ceramic spacer 701 has a recessed portion 701*a* engaged with the tip end 30 of heater 3.

Interposing the ceramic spacer between the tip end 301 of heater 3 and bottom surface 201 of sensor element 2 is effective to absorb shock.

Figure 33:
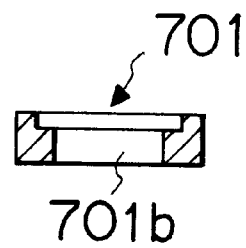
FIG. 33 is a cross-sectional view showing another example of the spacer shown in FIG. 31B.

As shown in FIG. 33, it is possible to use a ceramic spacer 701 having a through hole 701*b*. Reducing the heat capacity of ceramic spacer 701 is effective to suppress the reduction of efficiency in heating sensor element 2 by heater 3.

Tenth Embodiment

Figure 34:
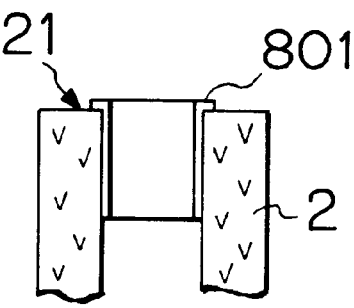
FIG. 34 is a cross-sectional view showing a guide plate in accordance with a tenth embodiment of the present invention.
Figure 35:
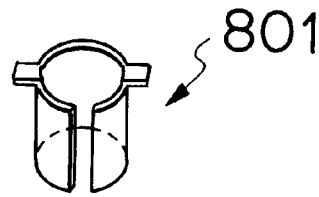
FIG. 35 is a perspective view showing the guide plate shown in FIG. 34.

A tenth embodiment of the present invention discloses an engagement between metallic holder 4 and sensor element 2, as shown in FIGS. 34 and 35.

A guide plate 801 is disposed beforehand at the open end 21 of sensor element 2 at the inside wall portion where metallic holder 4 is fixed. Then, metallic holder 4 similar to that shown in FIG. 12A is guided and fixedly inserted into this guide plate 801.

Guide plate 801 can be formed from a metal plate by bending this metal plate into a cylindrical shape as shown in FIG. 35.

According to the tenth embodiment, the open end 21 of sensor element 2 can be protected by guide plate 801 during the installation of heater 3 into inside chamber 20 of sensor element 2. Thus, it becomes possible to prevent the edge of sensor element 2 from being cracked or damaged. It is advantageous in speeding up the assembling operation.

Furthermore, it is preferable to apply surface treatment on the inside surface of guide plate 801 to allow metallic holder 4 to slide smoothly.

As this invention may be embodied in several forms without departing from the spirit of essential characteristics thereof, the present embodiments as described are therefore intended to be only illustrative and not restrictive, since the scope of the invention is defined by the appended claims rather than by the description preceding them, and all changes that fall within the metes and bounds of the claims, or equivalents of such metes and bounds, are therefore intended to be embraced by the claims.

What is claimed is:

1. An air-fuel ratio sensor comprising:
   a cylindrical solid electrolytic element having an open end and an opposed closed end with an inside chamber defined therein;
   an inside electrode provided on an inner surface of said solid electrolytic element;
   an outside electrode provided on an outer surface of said solid electrolytic element;
   a heater accommodated in said inside chamber so as to extend in an axial direction for warming up said solid electrolytic element to a predetermined active temperature level; and
   a metallic holder having a single heater holding portion supporting said heater at only one portion thereof in an axial direction, a fixing portion elastically deformable in radial directions and directly engaged with said solid electrolytic element, and a flange portion extending radially outward from said fixing portion, said flange portion having an outer diameter larger than an inner diameter of said solid electrolytic element so as to serve as a stopper for positioning said metallic holder at said open end of said solid electrolytic element when said metallic holder is inserted in the axial direction along said inner surface of said solid electrolytic element, thereby preventing said metallic holder from entering deeply into said inside chamber of solid electrolytic element.

2. The air-fuel ratio sensor in accordance with claim 1, wherein said fixing portion is electrically connected to said inside electrode, and an output signal of said inside electrode is taken out via a lead piece integrally extending in the axial direction from said fixing portion.

3. The air-fuel ratio sensor in accordance with claim 2, wherein said heater has two opposed lead wires on a surface thereof, and said lead piece integrally extending from said fixing portion is angularly shifted by approximately 90° from each of said two opposed lead wires.

4. The air-fuel ratio sensor in accordance with claim 2, wherein said lead piece integrally extending from said fixing portion is configured into a flat plate shape.

5. The air-fuel ratio sensor in accordance with claim 1, wherein a front end of said heater is brought into contact with a bottom surface of said inside chamber formed by an inside surface of said opposed closed end of said solid electrolytic element.

6. The air-fuel ratio sensor in accordance with claim 1, wherein said metallic holder is made of a metallic plate, and each of said heater holding portion and said fixing portion is formed into an open cylindrical shape with a slit by bending said metallic plate so as to have a C-shaped ring cross section along a plane normal to said axial direction.

7. The air-fuel ratio sensor in accordance with claim 6, wherein each slit of said heater holding portion and said fixing portion is aligned on a same axial line.

8. The air-fuel ratio sensor in accordance with claim 1, wherein said heater holding portion and said fixing portion are integrally connected via a connecting portion.

9. The air-fuel ratio sensor in accordance with claim 8, wherein said connecting portion is a neck portion narrower than said heater holding portion and said fixing portion.

10. The air-fuel ratio sensor in accordance with claim 1, wherein said heater has a rectangular cross section.

11. The air-fuel ratio sensor in accordance with claim 1, wherein said heater has a through hole extending in the axial direction.

12. The air-fuel ratio sensor in accordance with claim 1, wherein said fixing portion of said metallic holder is elastically expandable in radially outward directions so that said fixing portion is engaged with the inside surface of said solid electrolytic element by a resilient force caused by said fixing portion.

13. The air-fuel ratio sensor in accordance with claim 1, wherein said fixing portion of said metallic holder is elastically expandable in radially inward directions so that said fixing portion is engaged with the outside surface of said solid electrolytic element by a resilient force caused by said fixing portion.

14. An air-fuel ratio sensor comprising:
   a cylindrical solid electrolytic element having an open end and an opposed closed end with an inside chamber defined therein;
   an inside electrode provided on an inner surface of said solid electrolytic element;
   an outside electrode provided on an outer surface of said solid electrolytic element;
   a heater accommodated in said inside chamber so as to extend in an axial direction for warming up said solid electrolytic element to a predetermined active temperature level; and
   a metallic holder having a single heater holding portion and a fixing portion integrally formed by an elastically deformable metallic plate, wherein said heater holding portion has a cylindrical shape formed by bending said metallic plate to have a C-shaped cross section for supporting said heater at only one portion thereof in an axial direction, and said fixing portion has a cylindrical shape formed by bending said metallic plate to have a C-shaped cross section larger than said C-shaped cross section of said heater holding portion so as to be elastically expandable in radial directions and directly elastically engaged with the inner surface of said solid electrolytic element at a position axially offset from said heater holding portion, with opposing parallel straight edges of said fixing portion extending in the axial direction with a predetermined clearance therebetween.

15. The air-fuel ratio sensor in accordance with claim 14, wherein each of said opposing parallel straight edges of said fixing portion is continuous to a tapered leading end portion serving as a guide for inserting said metallic holder in the axial direction along said inner surface of said solid electrolytic element, so that a clearance between opposed edges of said fixing portion is gradually widened at a leading end of said fixing portion.

16. An air-fuel ratio sensor comprising:
a cylindrical solid electrolytic element having an open end and an opposed closed end with an inside chamber defined therein;
an inside electrode provided on an inner surface of said solid electrolytic element;
an outside electrode provided on an outer surface of said solid electrolytic element;
a heater accommodated in said inside chamber so as to extend in an axial direction for warming up said solid electrolytic element to a predetermined active temperature level; and
a metallic holder having a heater holding portion, a fixing portion, and a flange portion which are integrally formed by an elastically deformable metallic plate,
wherein said heater holding portion has a cylindrical shape formed by bending said metallic plate to have a C-shaped cross section for supporting said heater at only one portion thereof in an axial direction,
said fixing portion has a cylindrical shape formed by bending said metallic plate to have a C-shaped cross section larger than said C-shaped cross section of said heater holding portion so as to be elastically expandable in radial directions and directly elastically engaged with the inner surface of said solid electrolytic element at a position axially offset from said heater holding portion, with opposing parallel straight edges of said fixing portion extending in the axial direction with a predetermined clearance therebetween, and
said flange portion extends radially outward from said fixing portion and has an outer diameter larger than an inner diameter of said solid electrolytic element so as to serve as a stopper for positioning said metallic holder at said open end of said solid electrolytic element when said metallic holder is inserted in the axial direction along said inner surface of said solid electrolytic element, thereby preventing said metallic holder from entering deeply into said inside chamber of solid electrolytic element.

17. The air-fuel ratio sensor in accordance with claim 16, wherein each of said opposing parallel straight edges of said fixing portion is continuous to a tapered leading end portion serving as a guide for inserting said metallic holder in the axial direction along said inner surface of said solid electrolytic element, so that a clearance between opposed edges of said fixing portion is gradually widened at a leading end of said fixing portion.

18. The air-fuel ratio sensor in accordance with claim 16, wherein said fixing portion is electrically connected to said inside electrode, and an output signal of said inside electrode is taken out via a lead piece integrally extending in the axial direction from said fixing portion.

19. The air-fuel ratio sensor in accordance with claim 18, wherein said heater has two opposed lead wires on a surface thereof, and said lead piece integrally extending from said fixing portion is angularly shifted by approximately 90° from each of said two opposed lead wires.

20. The air-fuel ratio sensor in accordance with claim 18, wherein said lead piece integrally extending from said fixing portion is configured into a flat plate shape.

21. The air-fuel ratio sensor in accordance with claim 16, wherein a front end of said heater is brought into contact with a bottom surface of said inside chamber formed by an inside surface of said opposed closed end of said solid electrolytic element.

22. The air-fuel ratio sensor in accordance with claim 16, wherein said metallic holder is made of a metallic plate, and each of said heater holding portion and said fixing portion is formed into an open cylindrical shape with a slit by bending said metallic plate so as to have a C-shaped ring cross section along a plane normal to said axial direction.

23. The air-fuel ratio sensor in accordance with claim 22, wherein each slit of said heater holding portion and said fixing portion is aligned on a same axial line.

24. The air-fuel ratio sensor in accordance with claim 16, wherein said heater holding portion and said fixing portion are integrally connected via a connecting portion.

25. The air-fuel ratio sensor in accordance with claim 24, wherein said connecting portion is a neck portion narrower than said heater holding portion and said fixing portion.

26. The air-fuel ratio sensor in accordance with claim 16, wherein said heater has a rectangular cross section.

27. The air-fuel ratio sensor in accordance with claim 16, wherein said heater has a through hole extending in the axial direction.

28. The air-fuel ratio sensor in accordance with claim 16, wherein said fixing portion of said metallic holder is elastically expandable in radially outward directions so that said fixing portion is engaged with the inside surface of said solid electrolytic element by a resilient force caused by said fixing portion.

29. The air-fuel ratio sensor in accordance with claim 16, wherein said fixing portion of said metallic holder is elastically expandable in radially inward directions so that said fixing portion is engaged with the outside surface of said solid electrolytic element by a resilient force caused by said fixing portion.

* * * * *